United States Patent
Moskal

(10) Patent No.: US 9,198,948 B2
(45) Date of Patent: *Dec. 1, 2015

(54) METHODS OF TREATING DEPRESSION AND OTHER RELATED DISEASES

(71) Applicant: Northwestern University

(72) Inventor: Joseph Moskal, Evanston, IL (US)

(73) Assignee: Northwestern University, Evaston, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/937,986

(22) Filed: Jul. 9, 2013

(65) Prior Publication Data

US 2013/0310323 A1 Nov. 21, 2013

Related U.S. Application Data

(63) Continuation of application No. 13/909,712, filed on Jun. 4, 2013, which is a continuation of application No. 13/608,556, filed on Sep. 10, 2012, now Pat. No. 8,492,340, which is a continuation of application No. 13/440,368, filed on Apr. 5, 2012, which is a continuation-in-part of application No. PCT/US2010/051415, filed on Oct. 5, 2010.

(60) Provisional application No. 61/248,650, filed on Oct. 5, 2009, provisional application No. 61/471,942, filed on Apr. 5, 2011, provisional application No. 61/507,252, filed on Jul. 13, 2011.

(51) Int. Cl.
| | |
|---|---|
| *A61K 38/07* | (2006.01) |
| *A61K 45/06* | (2006.01) |
| *C07K 5/083* | (2006.01) |
| *C07K 5/097* | (2006.01) |
| *C07K 5/103* | (2006.01) |
| *C07K 5/078* | (2006.01) |

(52) U.S. Cl.
CPC ............. *A61K 38/07* (2013.01); *A61K 45/06* (2013.01); *C07K 5/06139* (2013.01); *C07K 5/081* (2013.01); *C07K 5/0821* (2013.01); *C07K 5/1013* (2013.01)

(58) Field of Classification Search
CPC .............................. A61K 38/07; A61K 45/06
See application file for complete search history.

(56) References Cited

U.S. PATENT DOCUMENTS

| | | | |
|---|---|---|---|
| 4,904,681 A | 2/1990 | Cordi et al. |
| 4,959,493 A | 9/1990 | Ohfume et al. |
| 5,061,721 A | 10/1991 | Cordi et al. |
| 5,086,072 A | 2/1992 | Trullas et al. |
| 5,166,136 A | 11/1992 | Ward et al. |
| 5,350,769 A | 9/1994 | Kasai et al. |
| 5,523,323 A | 6/1996 | Maccecchini |
| 5,605,911 A | 2/1997 | Olney et al. |
| 5,648,259 A | 7/1997 | Mallet et al. |
| 5,741,778 A | 4/1998 | Martin et al. |
| 5,763,393 A | 6/1998 | Moskal et al. |
| 5,804,550 A | 9/1998 | Bourguignon |
| 5,837,730 A | 11/1998 | Javitt |
| 5,902,815 A | 5/1999 | Olney et al. |
| 5,952,389 A | 9/1999 | Fogel |
| 5,959,075 A | 9/1999 | Lok et al. |
| 6,007,841 A | 12/1999 | Caruso |
| 6,017,957 A | 1/2000 | Skolnick et al. |
| 6,025,471 A | 2/2000 | Deghenghi |
| 6,107,271 A | 8/2000 | Moskal et al. |
| 6,147,230 A | 11/2000 | Shimamoto et al. |
| 6,197,820 B1 | 3/2001 | Sontheimer et al. |
| 6,284,776 B1 | 9/2001 | Meltzer |
| 6,521,414 B2 | 2/2003 | Melcher et al. |
| 6,541,453 B2 | 4/2003 | Oldham et al. |
| 6,551,993 B1 | 4/2003 | Schneider |
| 6,635,270 B2 | 10/2003 | Hong et al. |
| 6,667,317 B2 | 12/2003 | Chenard et al. |
| 6,821,985 B2 | 11/2004 | Chenard et al. |
| 6,828,318 B2 | 12/2004 | Snape et al. |
| 7,273,889 B2 | 9/2007 | Mermelstein et al. |
| 7,884,080 B2 | 2/2011 | Aslanian et al. |
| 7,973,043 B2 | 7/2011 | Migaly |
| 8,492,340 B2 | 7/2013 | Moskal |
| 2003/0022253 A1 | 1/2003 | Moskal |
| 2003/0064921 A1 | 4/2003 | Millhauser et al. |
| 2003/0175734 A1 | 9/2003 | Kroes et al. |
| 2005/0037433 A1 | 2/2005 | Nakanishi et al. |
| 2005/0118286 A1 | 6/2005 | Suffin et al. |
| 2006/0241046 A1 | 10/2006 | Olivera et al. |
| 2007/0087404 A1 | 4/2007 | Stahl et al. |
| 2009/0221544 A1 | 9/2009 | Stein et al. |
| 2011/0306586 A1 | 12/2011 | Khan et al. |

(Continued)

FOREIGN PATENT DOCUMENTS

| | | |
|---|---|---|
| WO | WO-97/43306 A1 | 11/1997 |
| WO | WO-99/24584 A1 | 5/1999 |

(Continued)

OTHER PUBLICATIONS

NIMH-Bipolar Disorder. Published online 2013, pp. 1-9.*
Stahl, S. CNS Spectr., 2007, vol. 12, Issue 6, pp. 423-427.*
Lake et al. Curr. Opin. Psych., 2007, vol. 20, Issue 4, pgs. Abstract.*
Chilman-Blair et al. Drugs of the Future, 2003, Abstract.*
Abbott et al. (1995) "The Formalin Test: Scoring Properties of the First and Second Phases of the Pain Response in Rats," *Pain*, vol. 60, Issue 1, pp. 91-102.
Bennett et al. (1988) "A Peripheral Mononeuropathy in Rat That Produces Disorders of Pain Sensation Like Those Seen in Man," *Pain*, vol. 33, Issue 1, pp. 87-107.

(Continued)

*Primary Examiner* — Samira Jean-Louis
(74) *Attorney, Agent, or Firm* — Goodwin Procter LLP

(57) ABSTRACT

The invention relates to methods for treating depression, anxiety, and other related diseases by administering a peptide NMDAR partial agonist.

7 Claims, 18 Drawing Sheets

(56) References Cited

U.S. PATENT DOCUMENTS

| | | | |
|---|---|---|---|
| 2012/0178695 A1 | 7/2012 | Moskal | |
| 2012/0295852 A1 | 11/2012 | Moskal | |
| 2013/0005662 A1 | 1/2013 | Moskal | |
| 2013/0035292 A1 | 2/2013 | Moskal et al. | |
| 2013/0053325 A1 | 2/2013 | Moskal et al. | |

FOREIGN PATENT DOCUMENTS

| | | | |
|---|---|---|---|
| WO | WO-99/51985 A1 | 10/1999 | |
| WO | WO-00/28090 A2 | 5/2000 | |
| WO | WO-01/36685 A2 | 5/2001 | |
| WO | WO-01/96606 A2 | 12/2001 | |
| WO | WO-01/98367 A2 | 12/2001 | |
| WO | WO-02/47535 A2 | 6/2002 | |
| WO | WO-02/072609 A2 | 9/2002 | |
| WO | WO-03/010540 A1 | 2/2003 | |
| WO | WO-2009/039390 A2 | 3/2009 | |
| WO | WO 2009/105718 | 8/2009 | |
| WO | WO-2010/033757 A1 | 3/2010 | |
| WO | WO-2010/065709 A2 | 6/2010 | |
| WO | WO-2011/003064 A2 | 1/2011 | |
| WO | WO-2011/044089 A2 | 4/2011 | |

OTHER PUBLICATIONS

Burch et al. (2010) "GLYX-13, An NMDA Receptor Glycine Site Functional Partial Agonist, Does Not Elicit Psychotomimetic Side Effects in Normal Human Volunteers at Doses Expected to be Therapeutic in Treatment-Resistant Major Depressive Disorder," *NCDEU*, Jun. 16, 2010, Naurex, Inc. (1 page).

Burgdorf et al. (2008) "Uncovering the Molecular Basis of Positive Affect Using Rough-and-Tumble Play in Rats: A Role for the NMDA Receptor and Implications for Depression," (2 pages) (Poster #393. 1/UU11) *Neuroscience 2008*, Nov. 17, 2008.

Burgdorf et al. (2010) "The Antidepressant and Anxiolytic Properties of GLYX-13: A Novel NMDA Receptor Glycine Site Functional Partial Agonist," (Poster #198) *ACNP 2010*, Dec. 6, 2010 (1 page).

Burgdorf et al. (2011) "The N-Methyl-D-Aspartate Receptor Modulator GLYX-13 Enhances Learning and Memory, in Young Adult and Learning Impaired Aging Rats," *Neurobiol. Aging*, 32(4):698-706.

Forni (1998) "Two Diastereoisomers of 2-(Benzenesulfonyl)-5-benzoyl-1-oxo-3-phenyl-2,5-diazaspiro[3.4]octan-7-yl acetate," *Acta Crystallographica Section C: Crystal Structure Communications*, C54(9):1320-1322.

Foster et al. "Neurobiology: Taking Apart NMDA Receptors," *Nature*, vol. 329, Oct. 1987, pp. 395-396.

Golik (1972) "Synthesis of Malonimide Derivatives as Potential Penicillin Analogs," *J. Heterocycl. Chem.*, 9(1):21-4.

Grigg et al. (1995) "X=Y—ZH Systems as Potential 1,3-Dipoles. Part 46. Cascade 1,3-Dipolar Cycloaddition Reactions of Cephalosporin Imines," *Tetrahedron*, 51(48):13347-56.

Haring et al. "Binding Studies and Photoaffinity Labeling Identify Two Classes of Phencyclidine Receptors in Rat Brain," *Biochemistry*, vol. 26, 1987, pp. 5854-5861.

Haring et al. (1986) "Identification of Polypeptides of the Phencyclidine Receptor of Rat Hippocampus by Photoaffinity Labeling with [H3]Azidophencyclidine," *Biochemistry*, vol. 25, pp. 612-620.

Haring et al. (1987) "Multiple Mode of Binding of Phencyclidines: High Affinity Association Between Phencyclidine Receptors in Rat Brain and a Monovalent Ion-Sensitive Polypeptide," *Biochem. Biophys. Res. Comm.*, vol. 142, No. 2, pp. 501-510.

Haring et al. (1991) "Glycine-Like Modulation of N-Methyl-D-Aspartate Receptors by a Monoclonal Antibody that Enhances Long-Term Potentiation," *J. Neurochem.*, 57(1):323-332.

Johnson, et al. (1990) "Neuropharmacolgy of Phencyclidine: Basic Mechanisms and Therapeutic Potential," *Annu. Rev. Pharmacol. Toxicol.*, Vo. 30, pp. 707-750.

Khasanov et al. (2004) "Novel Asymmetric Approach to Proline-Derived Spiro-beta-lactams," *J. Org. Chem.*, 69(17):5766-5769.

Kloog et al. (1988) "Kinetic Characterization of the Phencyclidine-N-Methyl-d-asparate Receptor Interaction: Evidence for a Steric Blockade of the Channel," *Biochemistry*, vol. 27, Issue 3, pp. 843-848.

Kloog et al. (1988) "Mode of Binding of [3H]dibenzocycloalkenimine (MK-801) to the N-methylD-aspartate (NMDA) Receptor and its Therapeutic Implication," *FEBS Lett.*, vol. 230, Issue 1-2, pp. 167-170.

Koller et al. (2010) "Novel N-Methyl-D-aspartate Receptor Antagonists: A Review of Compounds Patented Since 2006," *Expert Opin. Ther. Patents*, 20(12):1683-1702.

Kroes et al. (2006) "Development of a Novel Glycobiologic Therapy for Glioblastoma," *Neuro-oncol.* 8(4):397-398, Oct. 2006, Abstract CB-14, 2 pages.

Kroes et al. (2006) "Development of a Novel Glycobiology-Based Therapeutic for Glioblastoma," *J. Neurochem.*, 99(Suppl. 1):17, Nov. 10, 2006, Abstract 50, 1 page.

Leander et al. (2010) "Lack of Ketamine-Like Discriminative Effects of GLYX-13: A Novel NMDA Receptor Glycine Site Functional Partial Agonist with Antidepressant-Like Preclinical Effects," *ACNP*, Dec. 2010, 218 (1 page).

Lynch et al. (2006) "Synaptic Pasticity in Early Aging," *Aging Research Reviews*, vol. 5, pp. 255-280.

Mayer et al. (1990) "Excitatory Amino Acid Receptors, Second Messengers and Regulation of Intracellular Ca2+ in Mammalian Neurons," *Trends in Pharmacol. Sci.*, vol. 11, pp. 254-260.

Mishra et al. (2002) "Three-Dimensional Quantitative Structure-Activity Relationship and Comparative Molecular Field Analysis of Dipeptide Hydroxamic Acid Helicobacter pylori Urease Inhibitors," *Antimicrob. Agents and Chemother.*, 46(8):2613-2618.

Monahan et al. (1989) "D-Cycloserine, a Positive Modulator of the N-Methyl-d-Asparate Receptor, Enhances Performance of Learning in Rats," *Pharm. Biochem. Behav.*, vol. 34, pp. 649-653.

Moskal, et al. (2009) "The anti-depressant and anxiolytic properties of GLYX-13: a Glycine-site Functional Partial Agonist (GFPA), a novel mechanism for modulating NMDA receptors," *ACNP Annual Meeting*, (Dec. 2009) (2 pages) (Abstract).

Moskal et al. (2009) "The Antidepressant and Anxiolytic Properties of GLYX-13: A Novel NMDA Receptor Glycine Site Functional Partial Agonist," (Poster #059) ACNP 2009, Dec. 7, 2009 (1 page).

Moskal et al. (1996) "Monoclonal Antibodies to the Dentate Gyrus: Immunocytochemical Characterization and Flow Cytometric Analysis of Hippocampal Neurons Bearing a Unique Cell-Surface Antigen," *J. Neurosci*, 6(7):2045-2053.

Moskal et al. (2001) "The Use of Antibody Engineering to Create Novel Drugs that Target N-Methyl-D-aspartate Receptors," *Current Drug Targets*, 2:331-345.

Moskal et al. (2005) "GLYX-13: A Monoclonal Antibody-Derived Peptide that Acts as an N-Methyl-D-aspartate Receptor Modulator," *Neuropharmacology*, 49:1077-1087.

Moskal et al. (2010) "A Novel Approach to Unlocking the Therapeutic Potential of the NMDA Receptor," *Vital Signs e-magazine*, Sep. 2010 (2 pages).

Narahashi et al. (2004) "Mechanisms of Action of Cognitive Enhancers on Neuroreceptors," *Biol. Pharm. Bull.*, Vo. 27, Issue 11, pp. 1701-1706.

Overman et al. (1985) "A Convenient Synthesis of 4-Unsubstituted beta-Lactams," *J. Am. Chem. Soc.*, 107(6):1698-701.

Raghavan et al. (2009) "Allosteric Modulation of the Dopamine D2 Receptor by Pro-Leu-Gly-NH2 Peptidomimetics Constrained in Either a Polyproline II Helix or a Type II beta-Turn Conformation," *J. Med. Chem.*, 52(7):2043-2051.

Ransom et al. (1988) "Cooperative Modulation of [3H]MK-801 Binding to the N-Methyl-d-Asparate Receptor-Ion Channel Complex by I-Glumate, Glycine, and Polyamines," *J. Neurochem.*, 51:830-836.

Rasmusson et al. (1973) "6-Substituted Penicillin Derivatives," VI. *Tetrahedron Lett.*, (2):145-8.

Siemion et al. (1988) "Conformational Preferences of the Sequential Fragments of the Hinge Region of the Human IgA1 Immunoglobulin Molecule," *Biophys. Chem.*, 31:35-44.

(56) References Cited

OTHER PUBLICATIONS

Stanton et al. (1987) "Inhibition of the Production and Maintenance of Long-Term Potentiation in Rat Hippocampal Slices by a Monoclonal Antibody," *Proc. Natl. Acad. Sci. USA*, 84:1684-1688.
Stanton et al. (2009) "Neuroprotection by a Novel NMDAR Functional Glycine Site Partial Agonist, GLYX-13," *Neuropharmacology and Neurotoxicology NeuroReport*, 00(00):1-5.
Tanwar et al. (2002) "Gene Expression Microarray Analysis Reveals YLK-40 to be a Potential Serum Marker for Malignant Character in Human Glioma," *Cancer Res.*, 62:4364-4368.
Thompson et al. (1992) "Hippocampus-Dependent Learning Facilitated by a Monoclonal Antibody or D-Cycloserine," *Nature*, 359:638-641.
Turturro et al. (1999) "Growth Curves and Survival Characteristics of the Animals Used in the Biomarkers of Aging Program," *Journal of Gerontology: Biological Sciences*, vol. 54A, No. 11, pp. B492-B501.
Wood (2005) "The NMDA Receptor Complex: A Long and Winding Road to Therapeutics," IDrugs, 8(3):229-235.
Wood et al. (2008) "Antinociceptive Action of GLYX-13: An N-Methyl-D-aspartate Receptor Glycine Site Partial Agonist," *NeuroReport*, 19(10):1061-1063.
Wood et al. (1989) "Tetrapeptide Inhibitors of the IgA1 Proteinases from Type I Neisseria gonorrhoeae," *J. Med. Chem.*, 32:2407-2411.
Zhang et al. (2008) "A NMDA Receptor Glycine Site Partial Agonist, GLYX-13, Simultaneously Enhances LTP and Reduces LTD at Schaffer Collateral-CA1 Synapses in Hippocampus," *Neuropharmacology*, 55:1238-1250.
Abramets, I.I., (2008) "Neurophysiological and Neurochemical Aspects of the Effects of Antidepressants and Mood Stabilizers," Neurophysiology, vol. 40, pp. 64-78.
Krystal, J.H., et al. (1999) "NMDA Agonists and Antagonists as Probes of Glutamatergic Dysfunction and Pharmacotherapies in Neuropsychiatric Disorders," Harvard Rev. Psychiatry, vol. 7, pp. 125-143.
Pittenger, C., et al. (2007) "The NMDA Receptor as a Therapeutic Target in Major Depressive Disorder," CNS & Neurological Diroders—Drug Targets, 6, pp. 101-115.
Abramets, I.I., "Neurophysiological and Neurochemical Aspects of the Effects of Antidepressants and Mood Stabilizers," Neurophysiology, vol. 40, 2008, pp. 64-78.
Krystal, J.H., et al., "NMDA Agonists and Antagonists as Probes of Glutamatergic Dysfunction and Pharmacotherapies in Neuropsychiatric Disorders," Harvard Rev. Psychiatry, vol. 7, 1999, pp. 125-143.
Abramets, I.I., "Neurophysiological and Neurochemical Aspects of the Effects of Antidepressants and Mood Stabilizers," *Neurophysiology*. (2008) 40:64-78.
Krystal, J.H., et al., "NMDA Agonists and Antagonists as Probes of Glutamatergic Dysfunction and Pharmacotherapies in Neuropsychiatric Disorders," Harvard Rev. Psychiatry, (1999) 7:125-143.
Pittenger, C., et al., "The NMDA Receptor as a Therapeutic Target in Major Depressive Disorder," CNS & Neurological Diroders—Drug Targets, (2007) 6:101-115.
Burgdorf et al. (2010) "The Antidepressant and Anxiolytic Properties of GLYX-13: a Novel NMDA Receptor Glycine Site Functional Partial Agonist," *Abstracts of the Annual Meeting of the Society for Neuroscience, Society for Neuroscience*. Jan. 1, 2010 (2 pages).
Extended European Search Report for EP10822514.5 dated Feb. 13, 2013.
Holderbach et al., (2006) "Enhanced Long-Term Synaptic Depression in an Animal Model of Depression," Biol. Psych. 62:92-100.
Burgdorf et al.(2008) "Uncovering the Molecular Basis of Positive Affect Using Rough-and-Tumble Play in Rats: A Role for the NMDA Receptor and Implications for Depression" (3 pages) (Poster #393. 1/UU11) Neuroscience 2008, Nov. 17, 2008—electronically available Sep. 2008.
Holderbach et al. (2007) "Enhanced Long-Term Synaptic Depression in an Animal Model of Depression" (9 pages) (62: pp. 92-100) Society of Biological Psychiatry, 2007.
M.J. Schell (2004) "The N-methyl D-aspartate receptor glycine site and D-serine metabolism: an evolutionary perpective," Phil. Trans. R. Soc. Lond. B. 359, 943-964.
Sugimoto et al. "Evidence for the involvement of $GABA_A$ receptor blockade in convulsions induced by cephalosporins." Neuropharmacology. (2003) 45:304-314.
Lopes et al. "Chronic Administration of NMDA Glycine Partial Agonists Induces Tolerance in the Porsolt Swim Test," *Pharmacology Biochemistry and Behavior*, 1997, vol. 58, No. 4, pp. 1059-1064.
Heresco-Levy et al. "Controlled Trial of D-Cycloserine Adjuvant Therapy for Treatment-Resistant Major Depressive Disorder," *Journal of Affective Disorders*, 2006, vol. 93, pp. 239-243.
Heresco-Levy et al. "A Randomized Add-On Trial of High-Dose D-Cycloserine for Treatment-Resistant Depression," *International Journal of Neuropsychopharmacology*, 2013, vol. 16, pp. 501-506.
"Use of antidepressants in schizophrenia" Br Med J. Apr. 12, 1980; 280(6220): 1037-1038.
International Search Report and Written Opinion for International Application No. PCT/US2012/35547, mailed Aug. 31, 2012, 12 pages.
International Preliminary Report on Patentability for International Application No. PCT/US2012/035547, mailed Apr. 3, 2014, 10 pages.
U.S. Appl. No. 13/330,368, filed Apr. 5, 2012, Methods of Treating Depression and Other Related Diseases.
U.S. Appl. No. 13/909,712, filed Jun.4, 2013, Methods of Treating Depression and Other Related Diseases.
U.S. Appl. No. 13/937,979, filed Jul. 9, 2013, Methods of Treating Depression and Other Related Diseases.
U.S. Appl. No. 13/937,999, filed Jul. 9, 2013, Methods of Treating Depression and Other Related Diseases.
U.S. Appl. No. 14/451,756, filed Aug. 5, 2014, Methods of Treating Depression and Other Related Diseases.

\* cited by examiner

TABLE 1

| Name SEQ ID NO | Amino Acid Sequence |
|---|---|
| NT-1: SEQ ID. NO:1. | Lys—Ala—Ser—Gln—Asp—Val—Ser—Thr—Thr—Val—Ala |
| NT-2: SEQ ID. NO:2. | Ser—Ala—Ser—Tyr—Arg—Tyr—Thr |
| NT-3: SEQ ID. NO:3. | Gln—Gln—His—Tyr—Ser—Thr—Pro—Pro—Thr |
| NT-4: SEQ ID. NO:4. | Val—Tyr—Tyr—Ser—Gln—Gln—His—Tyr—Ser—Thr—Pro—Pro—Thr |
| NT-5: SEQ ID. NO:5. | Glu—Asp—Leu—Ala—Val—Tyr—Tyr—Ser—Gln—Gln—His—Tyr—Ser—Thr—Pro—Pro—Thr |
| NT-6: SEQ ID. NO:6. | Ser—Val—Gln—Ala—Glu—Leu—Asp—Leu—Ala—Val—Tyr—Tyr—Ser—Gln—Gln—His—Tyr—Ser—Thr—Pro—Pro—Thr |
| NT-7: SEQ ID. NO:7. | Phe—Thr—Ile—Ser—Ser—Val—Gln—Ala—Glu—Leu—Asp—Leu—Ala—Val—Tyr—Tyr—Ser—Gln—Gln—His—Tyr—Ser—Thr—Pro—Pro—Thr |
| NT-8: SEQ ID. NO: 8. | Gln—Gln—His—Tyr—Ser—Thr—Pro—Pro—Thr—Phe—Gly—Gly—Gly |
| NT-9: SEQ ID. NO:9. | Gln—Gln—His—Tyr—Ser—Thr—Pro—Pro—Thr—Phe—Gly—Gly—Gly—Thr—Lys—Leu—Glu |
| NT-10: SEQ ID. NO:10 | Cys—Gln—Gln—His—Tyr—Ser—Thr—Pro—Pro—Thr—Cys<br>\_____ S——S _____/ |
| NT-11: SEQ ID. NO:11 | Ser—Gln—Gln—His—Tyr—Ser—Thr—Pro—Pro—Thr—Ser |
| NT-12: SEQ ID. NO:12 | Gln—Gln—His—Tyr—Ser |
| NT-13: SEQ ID. NO:13 | Thr—Pro—Pro—Thr |
| NT-14: SEQ ID. NO:14 | Thr—Pro—Pro |
| NT-15: SEQ ID. NO:15 | Pro—Pro—Thr |
| NT-16: SEQ ID. NO:16 | Pro—Pro |
| NT-17: SEQ ID. NO:17 | Thr—Pro—Thr |
| NT-18: SEQ ID. NO:18 | Thr |

FIGURE 1

METHODS OF TREATING DEPRESSION AND OTHER RELATED DISEASES

REFERENCE TO RELATED APPLICATIONS

This application is a continuation of U.S. Ser. No. 13/909,712 filed Jun. 4, 2013, which is a continuation of U.S. Ser. No. 13/608,556 filed Sep. 10, 2012, which is a continuation of U.S. Ser. No. 13/440,368 filed Apr. 5, 2012, which claims priority to U.S. Provisional Application No. 61/507,252, filed Jul. 13, 2011, and U.S. Provisional Application No. 61/471,942, filed Apr. 5, 2011, each of which is hereby incorporated by reference in its entirety. U.S. Ser. No. 13/440,368 is also a continuation-in-part of and claims priority to International Application No. PCT/US10/51415, filed Oct. 5, 2010, which claims priority to U.S. Provisional Application No. 61/248,650, filed Oct. 5, 2009, each of which is hereby incorporated by reference in its entirety.

BACKGROUND

The central nervous system (CNS) of mammals employs many neuroactive peptides to effect specialized signaling within the brain and spinal cord including the neuroactive peptides somatostatin, cholecystokinin, VIP, Substance P, enkephalin, Neuropeptide Y (NPY), Neurotensin, TRH, CCK, and dynorphin. (see generally The Biochemical Basis of Neuropharmacology, Cooper, Bloom and Roth, 5th ed., Oxford University Press, New York, 1986). The careful elucidation of the complex signaling pathways, which operate in the CNS, has led to identification of specific receptors modulated by these neuroactive peptides presenting important therapeutic targets for various disorders associated with the CNS.

The N-methyl-D-aspartate (NMDA) receptor (NMDAR), is one such receptor that has been implicated in neurodegenerative disorders including stroke-related brain cell death, convulsive disorders, and learning and memory. NMDAR also plays a central role in modulating normal synaptic transmission, synaptic plasticity, and excitotoxicity in the central nervous system. The NMDAR is further involved in Long-term potentiation (LTP). LTP is the persistent strengthening of neuronal connections that underlie learning and memory (See Bliss and Collingridge, 1993, Nature 361:31-39).

Two general classes of glutamate receptors have been characterized in the central nervous system (CNS). They are the metabotropic glutamate receptors, which belong to the G-protein coupled receptor family of signaling proteins, and the ionotropic glutamate receptors (Muir and Lees, Stroke, 1995, 26, 503-513). The ionotropic class is further subdivided into the AMPA, kainate, and NMDA receptor subtypes by the selective ligands that activate them.

Ionotropic glutamate receptors contain a ligand-gated ion channel, which serves as a modulator of synaptic transmission. The NMDA receptor (NMDAR) is unique in that it requires both glutamate and glycine for activation and subsequent opening of the ion channel (Mothet et al., Proc. Nat. Acad. Sci., 2000, 97, 4926-4931). Recent studies have demonstrated that the glycine site can serve to modulate the activity of glutamate synaptic transmission at the NMDAR. Thus, both the glutamate and glycine sites can be utilized for modulation of NMDAR activity.

The NMDAR is activated by the binding of NMDA, glutamate (Glu), and aspartate (Asp). It is competitively antagonized by D-2-amino-5-phosphonovalerate (D-AP5; D-APV), and non-competitively antagonized by phenylcyclidine (PCP), and MK-801. Most interestingly, the NMDAR is co-activated by glycine (Gly) (Kozikowski et al., 1990, Journal of Medicinal Chemistry 33:1561-1571). The binding of glycine occurs at an allosteric regulatory site on the NMDAR complex, and this increases both the duration of channel open time, and the frequency of the opening of the NMDAR channel.

Recent human clinical studies have identified NMDAR as a novel target of high interest for treatment of depression. These studies conducted using known NMDAR antagonists CPC-101,606 and ketamine have shown significant reductions in the Hamilton Depression Rating Score in patients suffering with refractory depression. Although, the efficacy was significant, but the side effects of using these NMDAR antagonists were severe.

NMDA-modulating small molecule agonist and antagonist compounds have been developed for potential therapeutic use. However, many of these are associated with very narrow therapeutic indices and undesirable side effects including hallucinations, ataxia, irrational behavior, and significant toxicity, all of which limit their effectiveness and/or safety.

Further, 50% or more of patients with depression do not experience an adequate therapeutic response to known administered drugs. In most instances, 2 or more weeks of drug therapy are need before meaningful improvement is observed, as noted in an open-label study on pharmacological treatment of depression. (Rush et al, Am. J. Psychiatry 2006, 163: 1905). There currently is no single effective treatment for depression, anxiety, and other related diseases.

Thus, there remains a need for improved treatments of depression, anxiety and/or other related diseases with compounds that provide increased efficacy and reduced undesirable side effects.

SUMMARY

The present invention provides methods for treating depression, anxiety, and other related diseases by administering a therapeutically effective dose of a GLYX peptide or derivative thereof having NMDAR partial agonist activity.

Accordingly, it is an object of the present invention to administer compounds that functionally interact with the glycine site of the NMDAR for the treatment of depression, anxiety, and other related diseases.

In one embodiment, the invention relates to administering a di-pyrrolidine peptide compound comprising the sequence Thr-Pro-Pro-Thr (SEQ ID NO: 13) exemplified by Formula I (GLYX-13) for the treatment of depression, anxiety, and other related diseases in mammals including humans.

Also provided herein is a method of acutely treating symptoms of depression in a patient in need thereof, comprising administering an effective amount of GLYX-13, for example, in a single unit dose. Such methods may relieve the patient of at least one symptom of depression about 2 weeks or less, 1 week or less, 1 day or less, 1 hour or less (e.g. 15 minutes or less, half an hour or less, after said administration.

Further provided herein is a method of treating refractory depression in a patient resistant to other antidepressants, wherein the patient is administered an effective amount of GLYX to alleviate at least one symptom of depression. In certain embodiments, the treatment-resistant patient is identified as one who has been treated with at least two types of antidepressant treatments prior to administration of GLYX-13. In other embodiments, the treatment-resistant patient is one who is identified as unwilling or unable to tolerate a side effect of at least one type of antidepressant treatment.

BRIEF DESCRIPTION OF FIGURES

FIG. 1 shows exemplary GLYX peptides;

DETAILED DESCRIPTION

Figure 2:
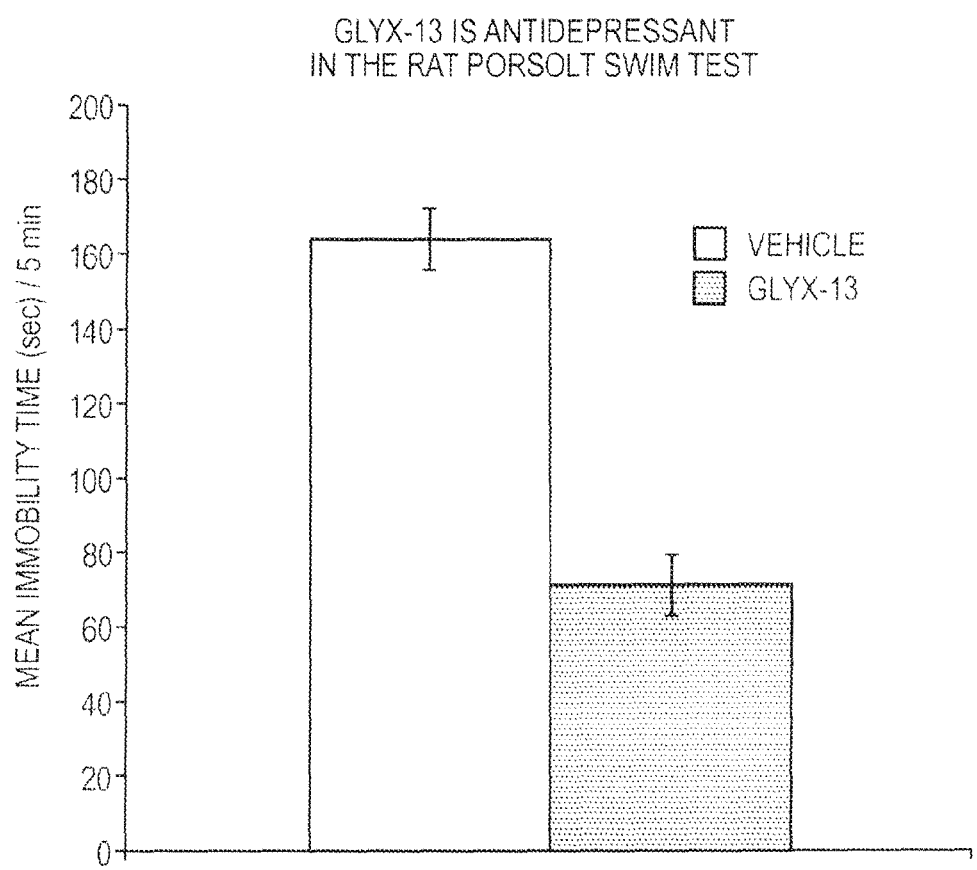
FIG. 2 shows the results of Porsolt tests conducted in order to access antidepressant action of GLYX-13.

Depression is a common psychological problem and refers to a mental state of low mood and aversion to activity. Various symptoms associated with depression include persistent anxious or sad feelings, feelings of helplessness, hopelessness, pessimism, and/or worthlessness, low energy, restlessness, irritability, fatigue, loss of interest in pleasurable activities or hobbies, excessive sleeping, overeating, appetite loss, insomnia, thoughts of suicide, and suicide attempts. The presence, severity, frequency, and duration of the above mentioned symptoms vary on a case to case basis. In some embodiments, a patient may have at least one, at least two, at least three, at least four, or at least five of these symptoms.

The most common depression conditions include Major Depressive Disorder and Dysthymic Disorder. Other depression conditions develop under unique circumstances. Such depression conditions include but are not limited to Psychotic depression, Postpartum depression, Seasonal affective disorder (SAD), mood disorder, depressions caused by chronic medical conditions such as cancer or chronic pain, chemotherapy, chronic stress, post traumatic stress disorders, and Bipolar disorder (or manic depressive disorder).

Refractory depression occurs in patients suffering from depression who are resistant to standard pharmacological treatments, including tricyclic antidepressants, MAOIs, SSRIs, and double and triple uptake inhibitors and/or anxiolytic drugs, as well non-pharmacological treatments such as psychotherapy, electroconvulsive therapy, vagus nerve stimulation and/or transcranial magnetic stimulation. A treatment resistant-patient may be identified as one who fails to experience alleviation of one or more symptoms of depression (e.g., persistent anxious or sad feelings, feelings of helplessness, hopelessness, pessimism) despite undergoing one or more standard pharmacological or non-pharmacological treatment. In certain embodiments, a treatment-resistant patient is one who fails to experience alleviation of one or more symptoms of depression despite undergoing treatment with two different antidepressant drugs. In other embodiments, a treatment-resistant patient is one who fails to experience alleviation of one or more symptoms of depression despite undergoing treatment with four different antidepressant drugs. A treatment-resistant patient may also be identified as one who is unwilling or unable to tolerate the side effects of one or more standard pharmacological or non-pharmacological treatment. In certain embodiments, the invention relates to methods for treating refractory depression by administering an effective amount of GLYX-13 to a treatment-resistant patient in need thereof. In an embodiment, methods of treating depression is contemplated when a patient has suffered depression for e.g. 5, 6, 7, 8 or more weeks, or for a month or more.

GLYX Peptides

As used herein, the term "GLYX peptide" refers to a peptide having NMDAR glycine-site partial agonist/antagonist activity. GLYX peptides may be obtained by well-known recombinant or synthetic methods such as those described in U.S. Pat. Nos. 5,763,393 and 4,086,196 herein incorporated by reference. Exemplary peptides are illustrated in FIG. 1. In some embodiments, GLYX refers to a tetrapeptide having the amino acid sequence Thr-Pro-Pro-Thr (SEQ ID NO: 13), or L-threonyl-L-prolyl-L-prolyl-L-threonine amide.

For example, GLYX-13 refers to the compound depicted as:

Formula I $$H_2N-\overset{\overset{\displaystyle \text{''}OH}{|}}{\text{C}}-\overset{O}{\text{C}}-N-\overset{O}{\text{C}}-N-\overset{O}{\text{C}}-\overset{\overset{\displaystyle OH}{|}}{\underset{H}{\text{N}}}-\overset{O}{\text{C}}-NH_2$$

Also contemplated are polymorphs, homologs, hydrates, solvates, free bases, and/or suitable salt forms of GLYX 13 such as, but not limited to, the acetate salt. The peptide may be cyclyzed or non-cyclyzed form as further described in U.S. Pat. No. 5,763,393. In some embodiments, an a GLYX-13 analog may include an insertion or deletion of a moiety on one or more of the Thr or Pro groups such as a deletion of $CH_2$, OH, or $NH_2$ moiety. In other embodiments, GLYX-13 may be optionally substituted with one or more halogens, $C_1$-$C_3$ alkyl (optionally substituted with halogen or amino), hydroxyl, and/or amino. Glycine-site partial agonist of the NMDAR are disclosed in U.S. Pat. No. 5,763,393, U.S. Pat. No. 6,107,271, and Wood et al., NeuroReport, 19, 1059-1061, 2008, the entire contents of which are herein incorporated by reference.

It may be understood that the peptides disclosed here can include both natural and unnatural amino acids, e.g., all natural amino acids (or derivatives thereof), all unnatural amino acids (or derivatives thereof), or a mixture of natural and unnatural amino acids. For example, one, two, three or more of the amino acids in GLYX-13 may each have, independently, a d- or l-configuration.

Methods

The present invention relates in part to the use of GLYX-13 for treatment of clinically relevant antidepressant and anxiolytic and for treatment of depression and anxiety in general.

GLYX-13 may act predominantly at NR2B-containing NMDARs, and may not display the classic side effects of known NMDAR modulators such as CPC-101,606 and ketamine. For example, in vitro studies show that GLYX-13 can markedly elevate long-term potentiation (LTP) while simultaneously reducing long-term depression (LTD) in rat hippocampal organotypic cultures. In some embodiments, GLYX-13 may produce an antidepressant effect essentially without dissociative side effects when administered to a subject in therapeutic amounts. In certain embodiments, an antidepressant effect with essentially no sedation may be produced by GLYX-13 when administered to a subject in therapeutic amounts. In still other embodiments, GLYX-13 may not have abuse potential (e.g., may not be habit-forming).

In some embodiments, GLYX-13 may increase AMPA GluR1 serine-845 phosphorylation. In certain embodiments, glycogen synthase kinase 3β (GSK-3β) may be activated by GLYX-13. In some cases, levels of β-catenin may be altered after administration of GLYX-13.

Additionally, GLYX-13 may have better Blood-Brain Barrier (BBB) penetration as compared to many of the earlier glycine site ligands (Leeson & Iversen, J. Med. Chem. 37:4053-4067, 1994) and may cross the BBB readily. In some embodiments, GLYX-13 or a composition comprising GLYX-13 may provide better i.v. in vivo potency and/or brain level concentration, relative to plasma levels.

Additionally, GLYX-13 may have a wide therapeutic index compared to other glycine site antagonists such as L-701,324, or other glycine site antagonists having narrow therapeutic indexes, which result in a very narrow range of dose between therapeutic effects and ataxia. For example, L-701,324 had anticonvulsant effects at doses that produced ataxia (Bristow, et al, JPET 279:492-501, 1996). Similarly, a series of Merz compounds had anticonvulsant effects at doses that produced ataxia (Parsons, et al., JPET283:1264-1275, 1997).

GLYX-13 may provide a high therapeutic index. For example, GLYX-13 may be therapeutically effective for depression and/or anxiety with an i.v. or subcutaneous dose range of about 1 to about 10 mg/kg, e.g. about 1 mg/kg, about 5 mg/kg, or about 10 mg/kg. In some embodiments, no ataxia occurs, at for example a dose of at 500 mg/kg, i.v.

The present invention relates at least in part to the use of a GLYX peptide or peptides alone or in combination with one or more other antidepressant treatments, such as, tricyclic antidepressants, MAO-I's, SSRI's, and double and triple uptake inhibitors and/or anxiolytic drugs for manufacturing a medicament for treating depression, anxiety, and/or other related diseases including provide relief from depression, anxiety and preventing recurrence of depression and anxiety. Exemplary drugs that may be used in combination with a GLYX peptide include Anafranil, Adapin, Aventyl, Elavil, Norpramin, Pamelor, Pertofrane, Sinequan, Surmontil, Tofranil, Vivactil, Parnate, Nardil, Marplan, Celexa, Lexapro, Luvox, Paxil, Prozac, Zoloft, Wellbutrin, Effexor, Remeron, Cymbalta, Desyrel (trazodone), and Ludiomill. It will be appreciated that in some embodiments, administration of GLYX-13 may act more quickly than a co-administered antidepressant treatment, and thus such co-administration (e.g., administration of GLYX-13 on an acute or immediate basis, while starting a regimen with another, slower acting antidepressant at about the same time) may be particularly advantageous in the common situation where the second antidepressant is slower acting.

Also contemplated herein are methods of treating depression that include administering GLYX peptides in combination with (e.g. simultaneously or sequentially) other non-pharmacological treatments such as psychotherapy, electroconvulsive therapy, vagus nerve stimulation and/or transcranial magnetic stimulation.

A variety of depression conditions are expected to be treated according to this aspect of the invention without affecting behavior or motor coordination, and without inducing or promoting seizure activity. Exemplary depression conditions that are expected to be treated according to this aspect of the invention include, but are not limited to, major depressive disorder, dysthymic disorder, psychotic depression, postpartum depression, premenstrual syndrome, premenstrual dysphoric disorder, seasonal affective disorder (SAD), anxiety, mood disorder, depressions caused by chronic medical conditions such as cancer or chronic pain, chemotherapy, chronic stress, post traumatic stress disorders, risk of suicide, and bipolar disorder (or manic depressive disorder). It should be understood that depression caused by bipolar disorder may be referred to as bipolar depression. In addition, patients suffering from any form of depression often experience anxiety. Various symptoms associated with anxiety include fear, panic, heart palpitations, shortness of breath, fatigue, nausea, and headaches among others. It is expected that the methods of the present condition can be used to treat anxiety or any of the symptoms thereof.

In addition, a variety of other neurological conditions are expected to be treated according to the methods of the invention. Exemplary conditions include, but are not limited to, a learning disorder, autistic disorder, attention-deficit hyperactivity disorder, Tourette's syndrome, phobia, post-traumatic stress disorder, dementia, AIDS dementia, Alzheimer's disease, Parkinson's disease, Huntington's disease, spasticity, myoclonus, muscle spasm, bipolar disorder, a substance abuse disorder, urinary incontinence, and schizophrenia.

Also provided herein are methods of treating depression in treatment resistant patients or treating refractory depression, e.g., patients suffering from a depression disorder that does not, and/or has not, responded to adequate courses of at least one, or at least two, other antidepressant compounds or therapeutics. For example, provided herein is a method of treating depression in a treatment resistant patient, comprising a) optionally identifying the patient as treatment resistant and b) administering an effective dose of GLYX-13 to said patient.

Provided herein, in an embodiment, are methods of acutely treating symptoms of depression in a patient in need thereof, comprising administering an effective amount of GLYX-13, for example, in a single unit dose. Such methods may relieve the patient of at least one symptom of depression for about 2 weeks or less, 1 week or less, 1 day or less, or 1 hour or less (e.g. 15 minutes or less, half an hour or less), after said administration. In some embodiments, such methods may relieve the patient of at least one symptom of depression for about 1 day or more, 1 week or more, or 2 weeks or more after said administration. For example, provided herein is a method comprising administering an effective amount of GLYX-13 to a patient suffering from depression, wherein said patient is substantially relieved of at least one symptom of depression substantially earlier after the first administration of GLYX-13, as compared to the same patient administered a non-GLYX-13 antidepressant compound. One of skill in the art will appreciate that such methods of acute administration may be advantageous in a hospital or out-patient setting.

Symptoms of depression, and relief of same, may be ascertained by a physician or psychologist, e.g. by a mental state examination. Symptoms include thoughts of hopelessness, self-harm or suicide and/or an absence of positive thoughts or plans.

Dosages

The dosage of any compositions of the present invention will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions of the present invention may be readily determined by techniques known to those of skill in the art or as taught herein.

A therapeutically effective amount of GLYX peptide required for use in therapy varies with the form of the depression condition being treated, the length of treatment time desired, the age and the condition of the patient, and is ultimately determined by the attending physician. In general, however, doses employed for adult human treatment typically are in the range of about 0.01 mg/kg to about 1000 mg/kg per day. The dose may be about 0.1 mg/kg to about 100 mg/kg per day. The desired dose may be conveniently administered in a single dose, or as multiple doses administered at appropriate intervals, for example as two, three, four or more sub-doses per day.

An effective dose or amount, and any possible affects on the timing of administration of the formulation, may need to be identified for any particular composition of the present invention. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions because the onset and duration of effect of the different agents may be complimentary.

Toxicity and therapeutic efficacy of subject compositions may be determined by standard pharmaceutical procedures in cell cultures or experimental animals, e.g., for determining the LD50 and the ED50.

The data obtained from the cell culture assays and animal studies may be used in formulating a range of dosage for use in humans. The dosage of any subject composition lies preferably within a range of circulating concentrations that include the ED50 with little or no toxicity. The dosage may vary within this range depending upon the dosage form employed and the route of administration utilized. For compositions of the present invention, the therapeutically effective dose may be estimated initially from cell culture assays.

Formulations

The GLYX peptides of the present invention may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations, or suppositories. For application by the ophthalmic mucous membrane route, compositions of the present invention may be formulated as eyedrops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

DNA encoding the GLYX peptides, incorporated into an expression vector, can also be administered, using any of the known administration methods, to express of the GLYX peptides in vivo.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, and patches.

For topical ocular administration compositions of this invention may take the form of solutions, gels, ointments, suspensions or solid inserts, formulated so that a unit dosage comprises a therapeutically effective amount of the active component or some multiple thereof in the case of a combination therapy.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

The present invention has multiple aspects, illustrated by the following non-limiting examples.

EXAMPLES

Antidepressant Action of GLYX-13 in Rats

Example 1

Methods

For the evaluation of the antidepressant actions of GLYX-13, the effect of GLYX-13 in the Porsolt test of depression was examined in rats. Porsolt testing is the most commonly used test for assessment of depression in animal model. Porsolt testing, also known as Forced Swim Test, is based on a behavioral trait that is sensitive to changes in affective state. During this test, the animal is placed in a tank (18 cm diameter×45 cm height) filled to 30 cm with 22-23° C. water. After placing the animal in the tank, the amount of time for which the rat is immobile when it stops struggling is measured. Porsolt test is based on the fact that antidepressants increase the latency to immobility and decrease the time for which the rat is immobile. In most of the cases, this occurs at antidepressant doses that do not increase locomotor activity on their own. The interpretation of the Porsolt test is that the antidepressants reinstate active coping mechanisms and decrease the passive immobility evoked by stress.

In order to evaluate the effectiveness of GLYX-13 as antidepressant, three month old FBNF1 rats were separated into two groups of 9 animals. The first group of rats was intravenously injected with 10 mg/kg GLYX-13 and the second group of animals was intravenously injected with PBS vehicle (1 ml/kg) in a blind manner via chronic subdural femoral vein access ports. Both groups of animals were injected 10 to 15 minutes before the start of testing.

For Porsolt testing, animals were given a 15 minute pre-test habituation in the tank to induce learned helplessness on day one. Following this, on the subsequent day, the animals were injected with GLYX-13 or vehicle 10-15 minutes before being placed into the tank for a 5 minute test session. After placing the animals in the tank, the amount of time for which each animal is immobile when it stops struggling (Mean Immobility Time) was measured. Decrease in Mean Immobility Time is a measure of the effectiveness of the antidepressant.

Results

As shown in FIG. 2, Mean Immobility Time of the group of animals pretreated with IV injections of PBS Vehicle (1 ml/kg) was higher compared to the Mean Immobility Time of the group of rats pretreated with IV injections of GLYX-13 (10 mg/kg) (FIG. 1). GLYX-13 produced an antidepressive-like effect in the Porsolt test with a 56.4±4.6% (Mean±SEM) reduction in floating compared to PBS vehicle (P<0.0001). Therefore, the data from the Porsolt test predicts effectiveness of GLYX-13 as antidepressant.

Example 2

Methods

A second experiment was performed in the same manner as Example 1, except that 2-3 month Sprague-Dawley rats were used, and treated with either intravenous (1, 3, 10, 32 mg/kg), subcutaneous (1,3, 10, 32, 56, 100 mg/kg) injections of GLYX-13 or saline vehicle (1 mg/ml) 15 (i.v.) or 20 (s.c.) min before the start of the final 5 min test session. Ketamine (10 mg/kg i.p.) was given 60 min before the start of testing (Garcia et al., (2008) Prog Neuropsychopharmacol Biol Psychiatry, 32, 140-144). Subcutaneous administration of 10 mg/kg ketamine followed by testing after 20 min post dosing produced severe dissociative side effects, as shown in FIG. 3.

Results

Figure 3:
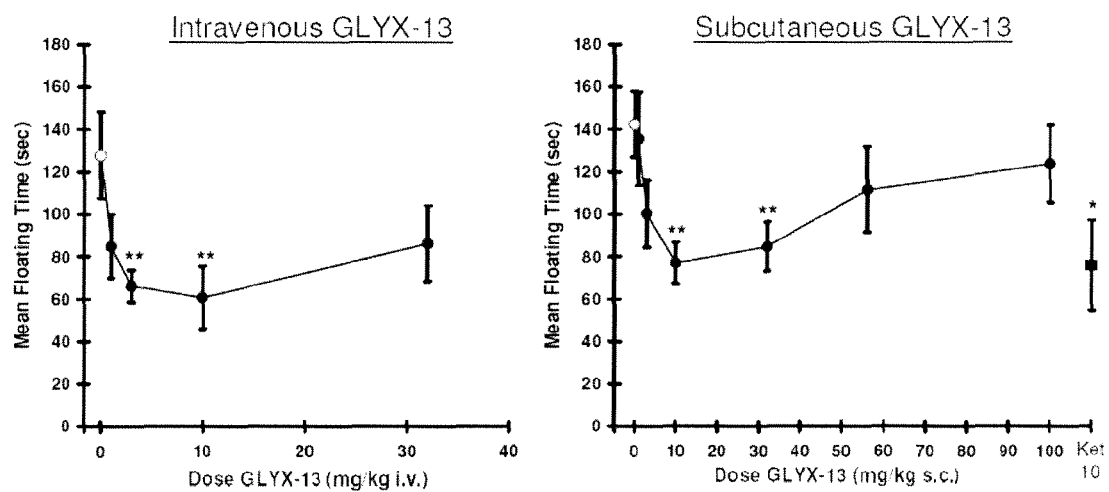
FIG. 3 shows the results of Porsolt tests conducted in order to access antidepressant action of GLYX-13 over a range of concentrations by either intravenous or subcutaneous administration.

Mean Immobility Time of the group of rats pretreated with IV injections or subcutaneous administration of PBS Vehicle was higher compared to the Mean Immobility Time of the group of rats pretreated with IV injections of GLYX-13 (FIG. 3; 0: 127.7±20.4; 2: 84.9±15.0; 3: 66.14±27.53; 10 60.6±14.7; 32: 87.19±17.85). GLYX-13 administered intravenously produced an antidepressive-like effect in the Porsolt test at all concentrations, with a 50±10% (Mean±SEM) maximum reduction in floating compared to saline vehicle (P<0.01). GLYX-13 administered subcutaneously produced an antidepressive-like effect in the Porsolt test at all concentrations, with a 43±7% (Mean±SEM) maximum reduction in floating compared to saline vehicle (P<0.01) (0: 142.4±15.6; 1: 135.5±22.0; 3: 100.2±15.7; 10: 76.9±9.7; 32: 84.7.19±11.6) Decrease in Mean Immobility Time is a measure of the effectiveness of the antidepressant; thus GLYX-13 functions as an antidepressant when administered intravenously or subcutaneously.

Example 3

Methods

Figure 4:
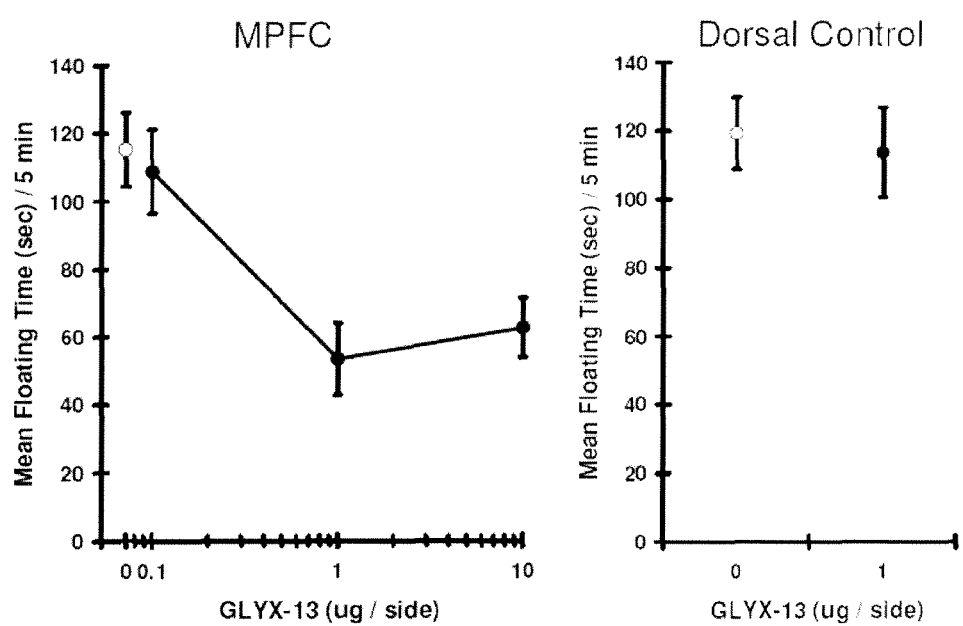
FIG. 4 shows the results of Porsolt tests conducted in order to access antidepressant action of GLYX-13 administered to the medial prefrontal cortex.

To determine whether GLYX-13 acts in an area of the brain that is clinically relevant for depression, GLYX-13 was administered to either the medial prefrontal cortex (MPFC), which is associated with mood and depression, or to the motor cortex (FIG. 4). Mean time spent immobile in the Porsolt test was determined for groups of 10 three-month old male Fisher Brown Norway F1 (FBNF1) rats pretreated with a single injection of GLYX-13 (1, 10 ug/side) or a single saline vehicle injection (0.5 ul/1 min) bilaterally into the medial prefrontal cortex or motor cortex (dorsal control) in animals with surgically implanted chronic indwelling cannulae aimed at the MPFC. Microinjections were made 1 week after surgery, and Porsolt testing was conducted 20 min post injection. Animals received a single 15 min training swim session one day before dosing.

Results

As shown in FIG. 4, GLYX-13 injected into the MPFC produced an antidepressive-like effect in the Porsolt test with a 50±5% (Mean±SEM) reduction in floating compared to a saline control or to GLYX-13 injected into motor cortex (dorsal control). (FIG. 4 0: 115.2±10.89; 0.1: 108.77±12.34; 1: 53.46±10.65; 10: 62.54±8.7; Dorsal Control Vehicle: 119.3±10.6; GLYX-13 113.7±13.1; Mean±SEM) These results indicate that the antidepressant effect of GLYX-13 may be mediated through the MPFC, an area of the brain associated with mood and depression.

Example 4

Methods

To determine whether the antidepressant effect of GLYX-13 was specific to the sequence of the GLYX-13 peptide, mean time (sec) spent floating in the Porsolt test was determined in groups of 12 three-month old Sprague Dawley rats administered with GLYX-13 (TPPT-NH2; 3 mg/kg, i.v. tail vein), a scrambled peptide (PTPT-NH3; 3 mg/kg i.v. tail vein), or 0.9% saline vehicle (1 ml/kg, i.v. tail vein). Administration occurred 60 min before the 5 min. testing session. Animals received a 15 min. training swim session one day before dosing.

Results

Figure 5:
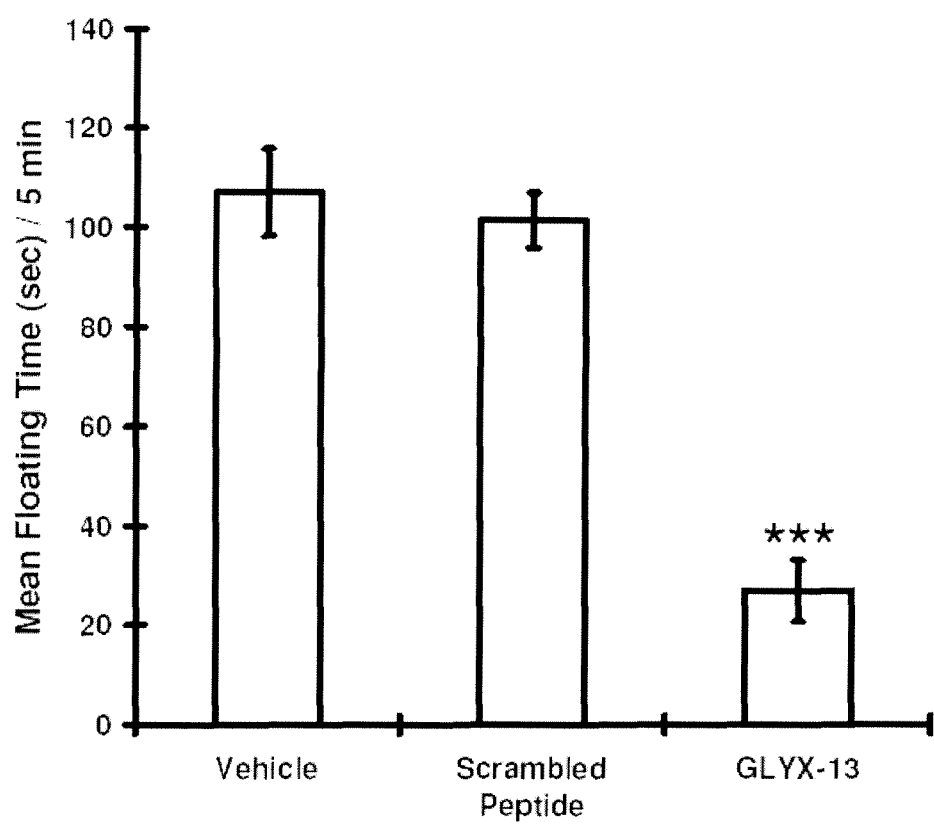
FIG. 5 shows the results of Porsolt tests conducted in order to evaluate the antidepressant action of GLYX-13 compared to a scrambled peptide.

Animals administered GLYX-13 showed a reduction in mean floating time of 70±5% (Mean±SEM) compared to animals receiving a saline injection or a scrambled peptide (FIG. 5). Therefore, the antidepressant effect is specific to GLYX-13 and does not represent an artifact of administering a peptide generally.

Discussion

The data depicted in FIGS. 2-5 show that GLYX-13 displays significant antidepressant-like properties in rats over a range of doses and routes of administration. In contrast to selective serotonin reuptake inhibitors (SSRIs), GLYX-13's onset of action was within minutes of a single dose. These results together with the recent clinical trials of known NMDAR molecules, and the fact that GLYX-13 has an outstanding therapeutic index, especially compared to other modulators of NMDA function, make GLYX-13 an attractive candidate for the treatment of depression.

These results show that NMDAR glycine-site partial agonists may be excellent therapeutic candidates for the treatment of depression.

Anxiolytic Action of GLYX-13

Example 5

The purpose of this study was to evaluate action of GLYX-13 on anxiety. In order to gauge the effect of GLYX-13 in rats, the open field test of anxiety was conducted. The open field test is a widely used neophobic test of anxiety (see, Treit D, Fundytus M. Thigmotaxis as a test for anxiolytic activity in rats. Pharmachol Biochem Behav 1989; 31:959-62.).

The open field area used for the open field test generally consists of an empty and bright square (or rectangular) arena, surrounded by walls. For the current study, an open field of 45 cm×35 cm×20 cm high was used. The rat was placed in the center of the arena and its behavior recorded over a predefined period of time (usually between 2 to 15 min). The open field test is based on the natural tendency of the rats to avoid open spaces. The open field test is based on the conflict between the innate anxiety that rats have of the central area of the open space versus their desire to explore new environments. When rats are in an anxious state, they have a natural tendency to stay near the walls. This natural tendency of the rats to stay close to the walls is called thigmotaxis. In this context, anxiety-related behavior is measured by the degree to which the rat avoids the center of the open field test. Determining the propensity of the rat to avoid the open field can be determined by measuring the number of center crosses made by the rats over a predefined interval of time, or by determining the amount of time the rat stays in the center of the field.

In order to evaluate the effectiveness of GLYX-13 as an anxiolytic, two groups of three month old FBNF1 rats were used. The first group was composed of 13 rats and the second group was composed of 11 rats. The first group of rats was intravenously injected with 10 mg/kg GLYX-13 and the second group of rats was intravenously injected with PBS vehicle (1 ml/kg) in a blind manner via chronic subdural femoral vein access ports. Both groups of rats were injected 10 to 15 minutes before the start of testing. After GLYX-13 injections, both groups of rats were tested in the open field.

For the open field test, rats were habituated to the open field for 2 minutes each day for three consecutive days before the final 2 minute test session in which GLYX-13 or vehicle was administered. Open field activity was recorded by a video camera mounted above the open field area, and number of center crosses in the open field was measured.

Results

Figure 6:
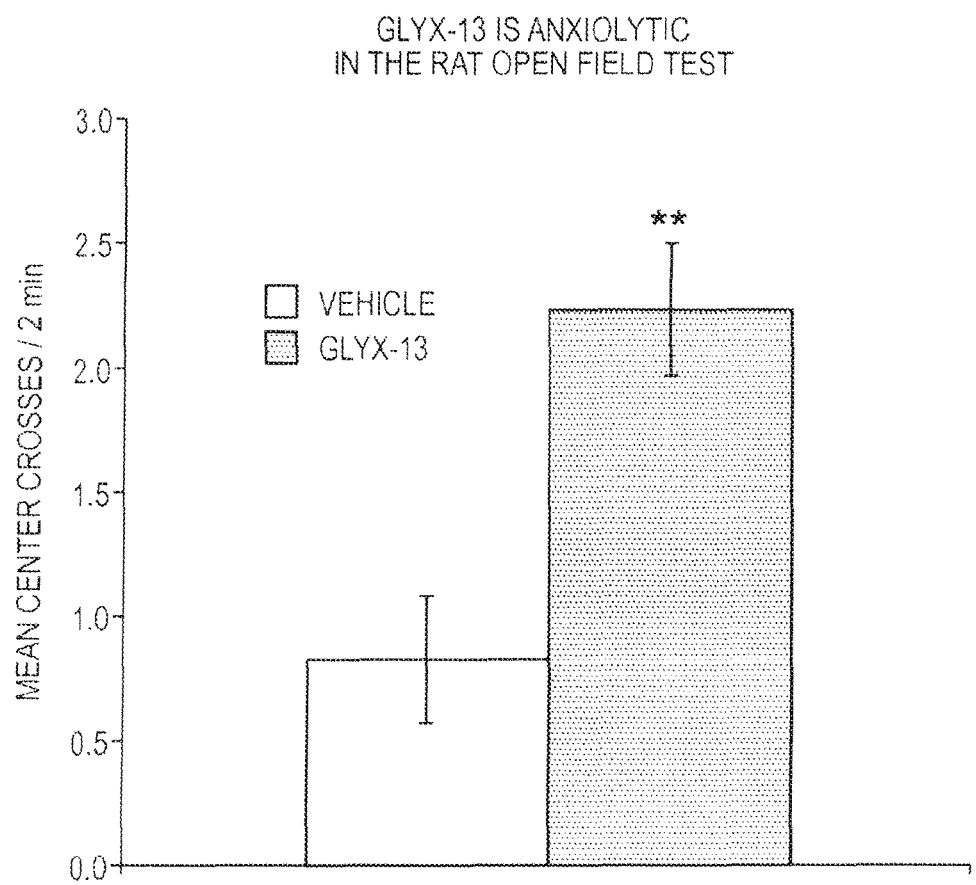
FIG. 6 shows the results of open field tests conducted in order to access anxiolytic action of GLYX-13.

Anxiolytic-like drug effects were measured by increased center crosses in the open field by the rats pretreated with IV injections of GLYX-13 (FIG. 6). GLYX-13 (10 mg/kg i.v.) produced an anxiolytic-like effect in the open field test with a 172.6±34.3% (Mean±SEM) increase in center crosses compared to vehicle (P<0.005).

Example 6

A second experiment was performed in the same manner as Example 3, except that groups of 8-10 two- to three-month old male Sprague-Dawley rats pretreated with either intravenous (1, 3, 10, 32 mg/kg), subcutaneous (1, 3, 10, 32, 56, 100 mg/kg) injections of GLYX-13, ketamine (10 mg/kg i.p.) or saline vehicle (1 mg/ml) 15 min (i.v.), 20 (s.c.) or 60 (i.p.) min before the start of the 5 min test session. Each data point represents a group of 8-10 rats. The average (mean) amount of time animals spent in the center of the field was measured.

Results

Figure 7:
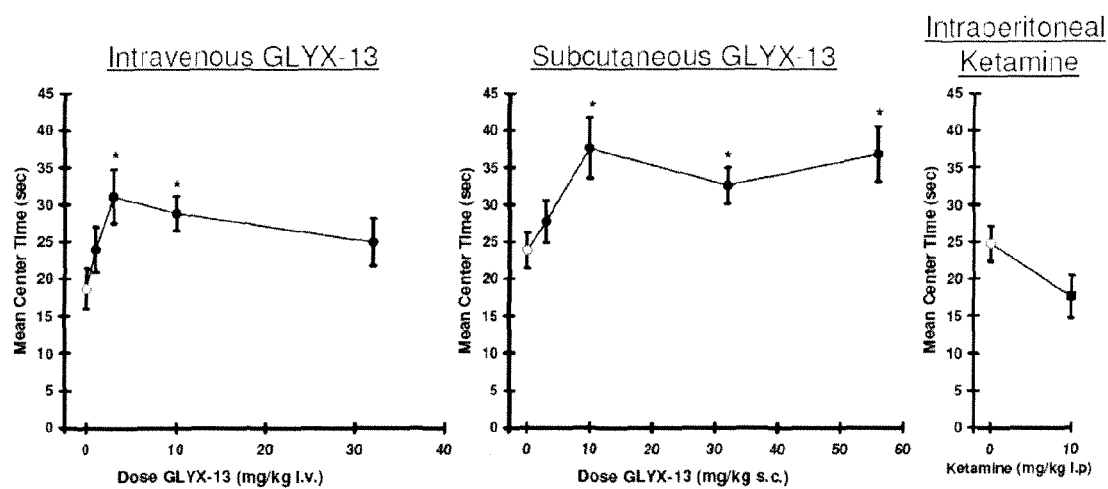
FIG. 7 shows the results of open field tests conducted in order to access anxiolytic action of GLYX-13 over a range of concentrations by either intravenous or subcutaneous administration.

Anxiolytic-like drug effects were measured by increased center crosses in the open field by the rats pretreated with IV or subcutaneous injections of GLYX-13 (FIG. 7). Intravenous GLYX-13 administration produced an anxiolytic-like effect in the open field test with a 42±5% (Mean±SEM) increase in the amount of time spent in the center of the field compared to vehicle (P<0.05). Subcutaneous GLYX-13 administration produced an anxiolytic-like effect in the open field test with a 36±5% (Mean±SEM) increase in the amount of time spent in the center of the field compared to vehicle (P<0.05).

Discussion

The data reported here show that GLYX-13 displays significant anxiolytic-like properties in rats over a range of doses and routes of administration. The results with GLYX-13 show that NMDAR glycine-site partial agonists may be excellent therapeutic candidates for the treatment of anxiety.

Evaluating Persistence of Action of the Anti-Depressive and Anxiolytic Effects of GLYX-13

Example 7

Methods

To evaluate whether the anti-depressive and anxiolytic effects of GLYX-13 would persist beyond a few hours, rats were tested in the Porsot test and the Open Field test, described above. Groups of 10-11 three-month old Sprague-Dawley rats were pretreated with GLYX-13 (3 mg/kg i.v.), ketamine (10 mg/kg i.v.) or saline vehicle injection (1 mg/ml i.v. tail vein) 96 hrs before the start of testing. Animals received a single 15 min. training swim session one day before dosing. Animals were tested 96 hrs post dosing in the Porsolt test without any testing during the intervening period. Open field testing was conducted without pre-habituation 1 day after Porsolt testing (i.e. 120 hrs post dosing). Mean (±SEM) time (sec.) spent floating in the Porsolt test, time spent in the center compartment (sec.), and line crosses in the open field test were determined.

Results

Figure 8:
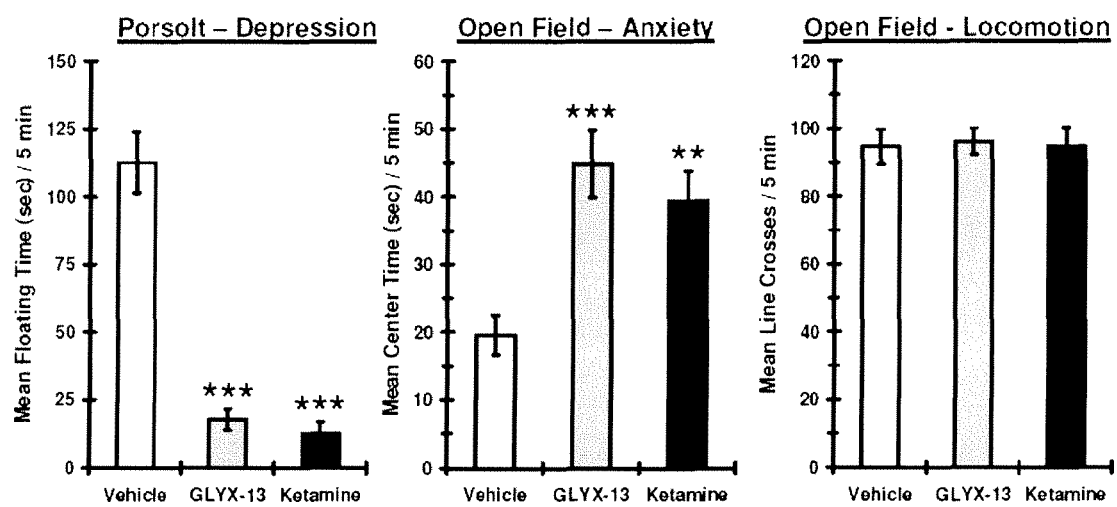
FIG. 8 shows the results of Porsolt tests and Open field tests conducted in order to determine the length of time the antidepressant and anxiolytic action of GLYX-13 persists.

Results of the Porsolt test showed that animals administered GLYX-13 showed an 82%±2 (mean±SEM) reduction in mean floating time compared to animals administered a saline control (FIG. 8, left panel). Results of the open field testing show that animals administered GLYX-13 showed an 125%±5 (mean±SEM) increase in mean center time compared to animals administered a saline control (FIG. 8, middle panel). Center time is a measure of anxiolysis. Line crossings are a measure of locomotor activity, and can be used as a control.

Discussion

These results show that the antidepressant effects of a single administration of GLYX-13 last up to 4 days, and that the anxiolytic effects persist up to 5 days. Thus, while the effects of GLYX-13 can be seen within minutes, the effect of a single administration also persists for at least several days.

Understanding the Molecular Underpinning of Rough-And-Tumble Play (RTP) Induced Positive Affect and Evaluation of Hedonic Effect of GLYX-13

Example 8

Understanding the Molecular Underpinning of RTP

In order to understand the molecular underpinning of RTP, four RTP sessions of 30 minutes each were conducted with rats. Control rats used for this study received identical handling as the RTP testing groups except that they were tested in isolation. Following these RTP sessions, frontal cortex and parietal cortex gene expression changes in rats were measured by microarray. These gene expression changes were examined 6 hours after the final of four 30 minutes RTP sessions.

Figure 9:
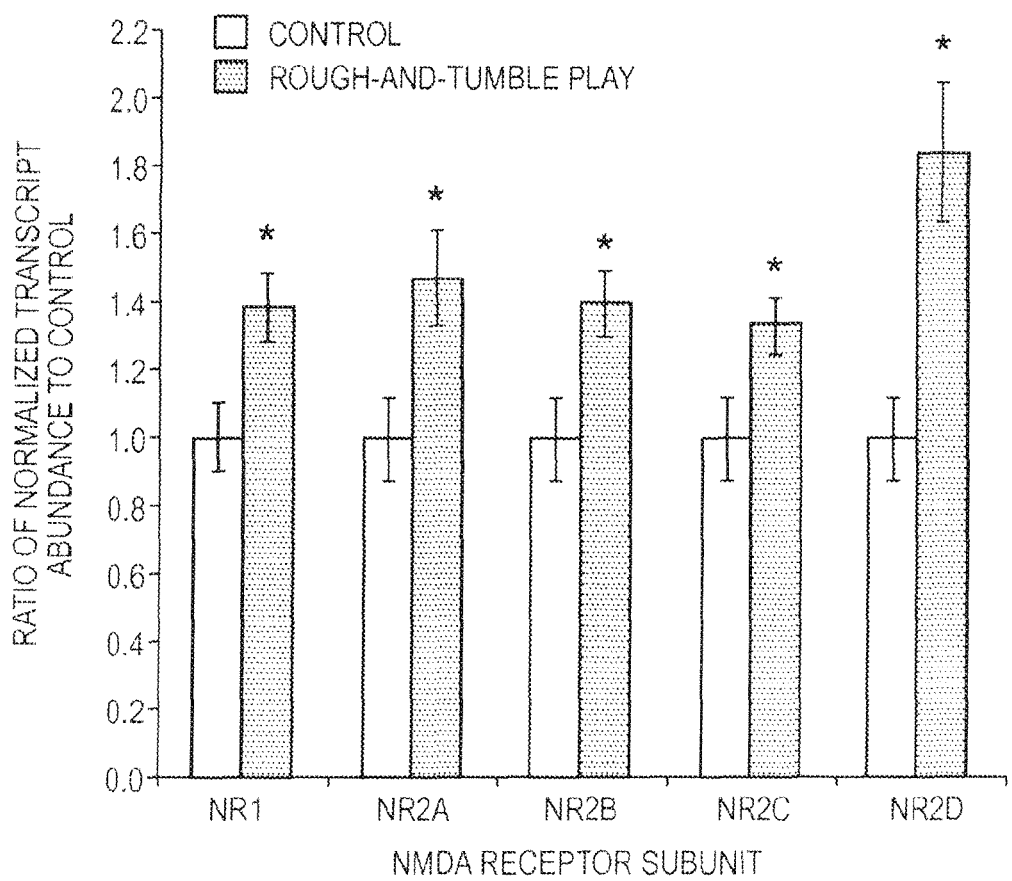
FIG. 9 shows qrt-PCR analysis of the NDMA Cortical mRNA Expression following Rough-and-Tumble play (RTP)

RTP increased expression of the NMDA family of genes (specifically: NMDA NR1, NR2AD subunits). The upregulation of NMDAR subunits was corroborated by qrt-PCR and the results have been presented in the FIG. 9.

Evaluation of Hedonic Effect of GLYX-13

To evaluate the hedonic effect of GLYX-13 in this study, the 50-kHz ultrasonic vocalizations model of positive affect was examined in rats (see, Burgdorf, J., Panksepp, J., Brudzynski, S. M., Kroes, R. A. & Moskal, J. R. (2008). The effect of selective breeding for differential rates of 50-kHz ultrasonic vocalizations on emotional behavior in rats. Devel. Psychobiology, 51, 34-46.).

Figure 10:
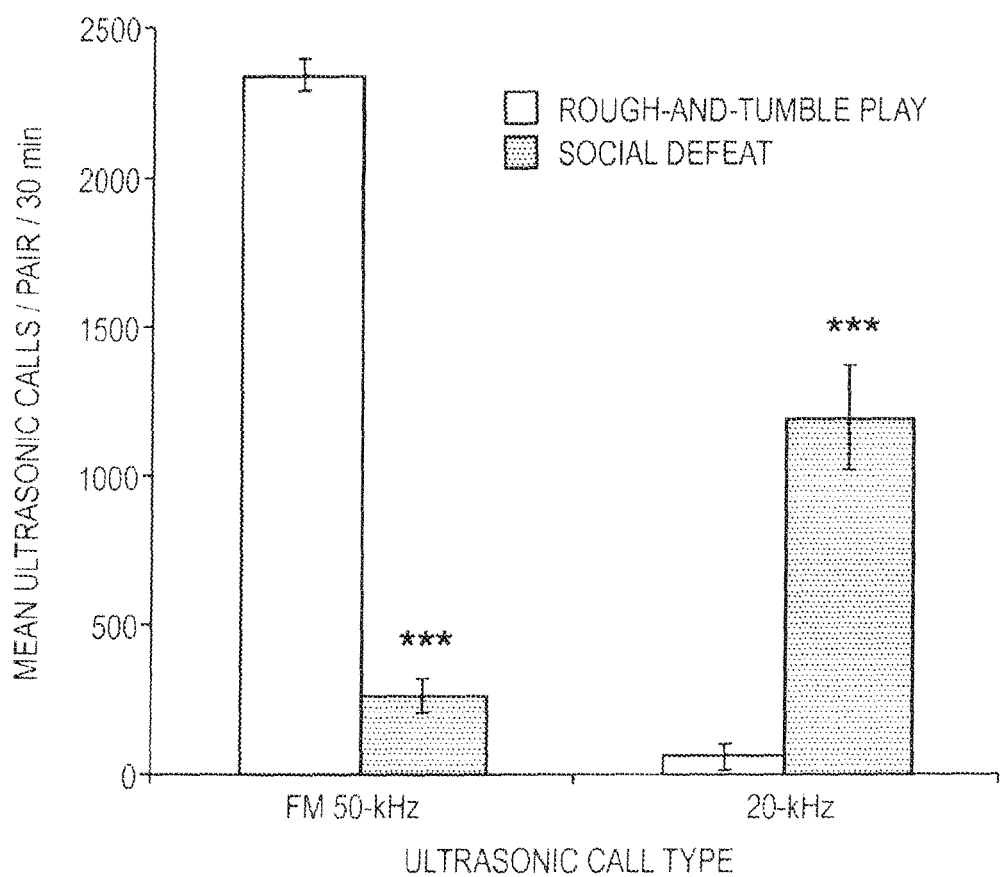
FIG. 10 shows RTP behavior elicits high rates of 50-kHz ultrasonic vocalizations and social defeat elicits high rates of aversive 22-kHz ultrasonic vocalizations.

According to 50-kHz ultrasonic vocalizations model of positive affect, RTP behavior in rats has been shown to be rewarding and to elicit high rates of 50-kHz ultrasonic vocalizations which in turn have been shown to reflect positive affective states (FIG. 10).

As a part of the study, two groups of three month old FBNF1 rats were used. The first group was composed of 13 rats and the second group was composed of 11 rats. The first group of rats was intravenously injected with 10 mg/kg GLYX-13 and the second group of rats was intravenously injected with PBS vehicle (1 ml/kg) in a blind manner via chronic subdural femoral vein access ports. Both groups of rats were injected 10 to 15 minutes before the start of test.

For hedonic ultrasonic vocalizations (USVs), animals received 2 minutes of heterospecific RTP habituation before the final 2 minutes test session.

Results

Figure 11:
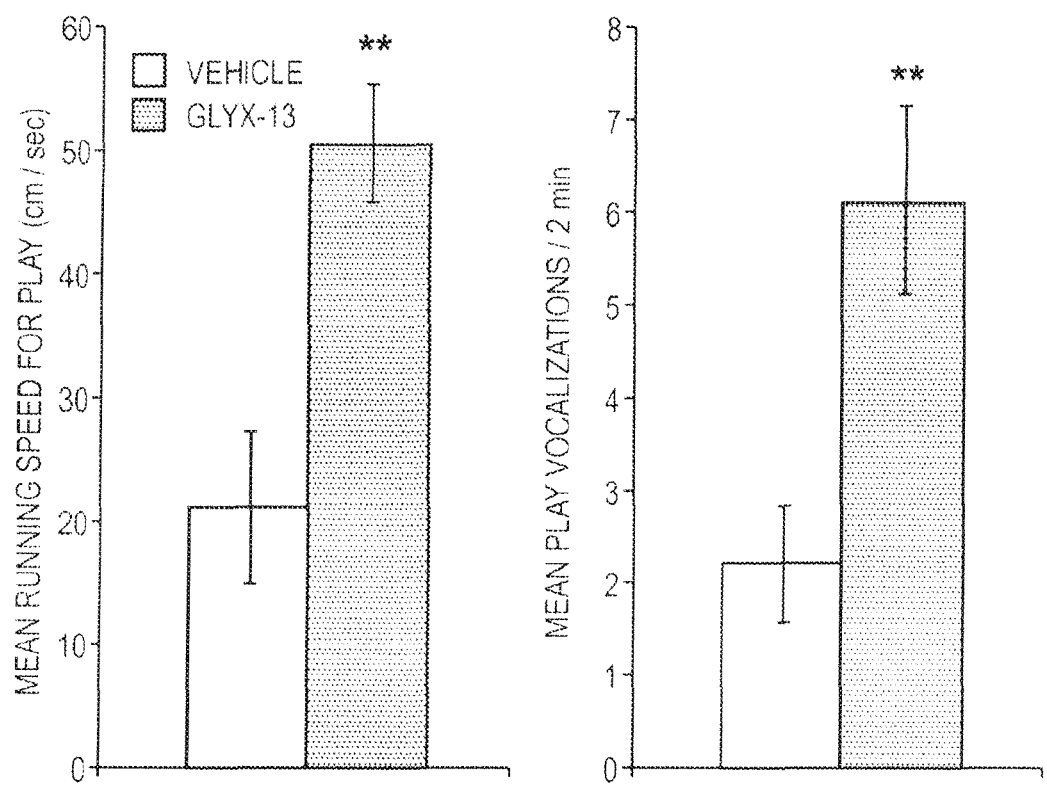
FIG. 11 shows effects of GLYX-13 on RTP in rats.

Direct injection of GLYX-13 dose (10 mg/kg i.v.) increased hedonic RTP induced 50-kHz ultrasonic vocalizations. GLYX-13 increased rates of play-induced positive affective 50-kHz USVs by 178.5±48.3% (Mean±SEM) compared to vehicle (P<0.01) (FIG. 11).

Discussion

These results suggest that the NMDA receptor may play a functional role in RTP-induced positive affective states. GLYX-13 may be a useful therapeutic to increase resilience to depression and anxiety.

Example 9

GLYX-13 Induces Rapid Antidepressant-Like Effects Essentially Without Dissociative Side Effects Adult male Sprague Dawley rats (Harlan, USA) were used for all studies except for the microinjection studies, for which Fisher Brown Norway F1 cross (FBNF1; Harlan, USA) rats were used. All rats were housed in Lucite cages with corn cob or sawdust bedding, maintained on a 12:12 light:dark cycle (lights on 8 AM), and given ad libitum access to Purina lab chow and tap water throughout the study. All experiments were approved by the Northwestern University, New York Medical College, or Virginia Commonwealth University Animal Care and Use Committees.

Porsolt Test

The Porsolt test adapted for use in rats was performed as above. Animals were placed in a 46 cm tall×20 cm in diameter clear plastic tube filled to 30 cm with tap water (23±1° C.) for 15 min on the first day (habituation) and 5 min on the subsequent test day.

Microinjection Studies

Bilateral 22-gauge guide cannulae (Plastic Products, USA) were stereotaxically implanted into the infralimbic/prelimbic cortex (+2.7 mm anterior, ±1.2 mm lateral, 3.1 mm ventral to bregma; cannulae angled 12° away from the midline) or dorsal control primary/secondary motor cortex (+2.7 mm anterior, ±1.2 mm lateral, 1.0 mm ventral to bregma; cannulae angled 12° away from the midline). Animals were allowed 1 week to recover from surgery before the start of testing. After the completion of behavioral testing, histology was conducted for cannulae tip location. For medial prefrontal cannulae, all tips were located within the infralimbic or prelimbic cortex 2.2-3.2 mm anterior to bregma. For motor cortex cannulae, all tips were located within the primary or secondary motor cortex 2.2-3.2 mm anterior to bregma.

Animals were trained with GLYX-13 (10 mg/kg, IV), ketamine (10 mg/kg, IV), or saline vehicle (1 mL/kg, IV) utilizing an unbiased two-chamber conditioned place preference apparatus.

Prepulse Inhibition

Animals were given intravenous injections of GLYX-13 (10 mg/kg) or saline via chronic indwelling femoral vein cannulae and tested 15 min post injection, or intraperitoneal ketamine (10 mg/kg) or saline vehicle (1 mL/kg IV or IP respectively) and tested immediately post injection for prepulse inhibition.

Drug Discrimination

Testing was conducted as described previously (Nicholson K L & Balster R L (2009) The discriminative stimulus effects of N-methyl-D-aspartate glycine-site ligands in NMDA antagonist-trained rats. Psychopharmacology (Berl) 203(2): 441-451). Adult male Sprague Dawley rats were trained to discriminate ketamine (10 mg/kg IP) from saline. Animals were then tested following various doses of GLYX-13 administration (3-156 mg/kg SC) and the percent of ketamine lever responding and rates of responding were recorded. Various doses of ketamine were tested as a positive control by both the IP and SC routes.

Protein Determinations

Total and Phosphoserine-9 glycogen synthase kinase 3β (GSK-3β) were quantified by ELISA according to the manufacturer's instructions (catalog numbers ADI-900-144 and ADI-900-123A, Assay Designs, USA). Total and phosphoserine-845 GluR1 were quantified by Western blot.

In Vitro Electrophysiology Experiments

Experiments were conducted on hippocampal slices from 14-18 day old Sprague-Dawley rats. Whole cell recordings were obtained from CA1 pyramidal neurons voltage clamped at −60 mV, in slices perfused with ACSF containing 0 mM [Mg2+] and 3 mM [Ca2+], plus 10 μM bicuculline and 20 μM CNQX to pharmacologically isolate NMDAR-dependent EPSCs. Following bath applications of varying concentrations of GLYX-13 and D-serine, EPSCs were elicited by stimulating Schaffer collateral fibers with single electrical pulses (80 μs duration) once every 30 s. NMDAR EPSCs were characterized by long rise and decay times, and were fully blocked at the end of each experiment by bath application of the NMDAR-specific antagonist D-2-amino-5-phosphonopentanoic acid (D-AP5; 50 μM).

Functional Affinity of GLYX-13

Functional affinity, Kp, of GLYX-13 for the NMDAR was estimated using the equiactive concentration null method of Stephenson (Stephenson R. P. (1956) A modification of receptor theory. Br J Pharmacol Chemother 11(4):379-393) as exemplified by Kenakin (Kenakin T. P. (1997) Pharmacologic Analysis of Drug-Receptor Interaction (New York))

Figure 18:
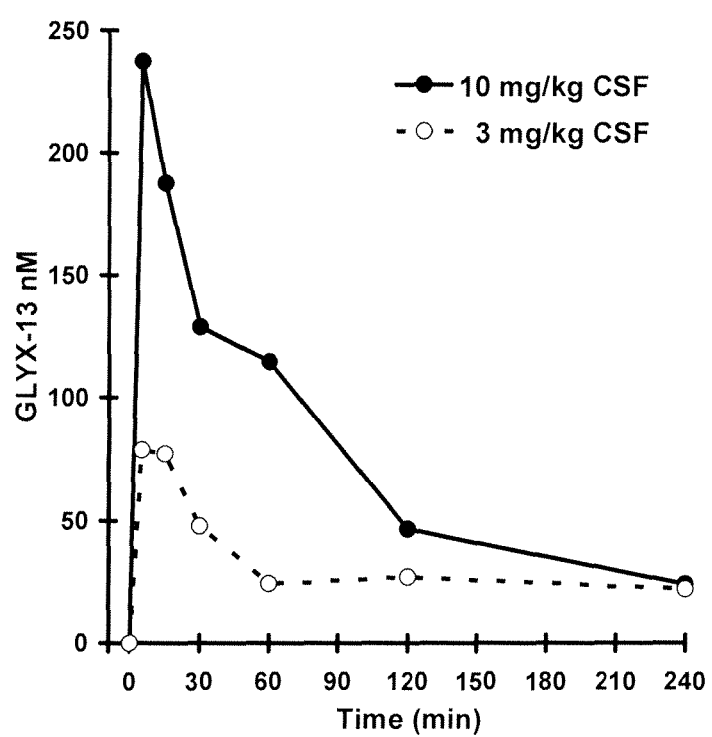
FIG. 18 shows a plot of cerebrospinal fluid (CSF) concentration of GLYX-13 versus time after administration.

In this analysis concentration-response curves are generated to full agonist, and to the full agonist in the presence of a set concentration of the partial agonist of interest (FIG. 18, Panel B). Equiactive concentrations are read off the ordinate of each of the concentration-response curves and plotted as the concentration of full agonist [D-serine] alone and in the presence of partial agonist [GLYX-13] that produce equal effect.

Bioanalysis

Male Sprague Dawley rats (250-300 g) received intravenous injections of GLYX-13 (3-10 mg/kg), briefly anesthetized with isoflurane, and cerebrospinal fluid (CSF) samples drawn and stored at −70 C. until analysis.

CSF samples were precipitated with internal standard Pro-Thr-Pro-Ser-NH2 in 400 μl of acetonitrile. Supernatant extract was separated by HPLC (LC-20AD, Shimadzu, Japan) using a Synergi 4μ Hydro-RP 8A column (Phenomenex, USA) with mobile phase of 100 mM ammonium formate with 0.1% formic acid for 0.1 minute followed by acetonitrile with 0.1% formic acid and samples were analyzed by LC-MS/MS (API4000, Applied Biosystems, USA) in ESI positive ion mode and the GLYX-13 (199.1 and 216.1) and IS (202.3) daughter ions quantified by multiple reaction monitoring. The lower limit of quantitation for the assay was 26.3 nM GLYX-13.

Results

Behavioral Pharmacology

Porsolt Test

Figure 12:
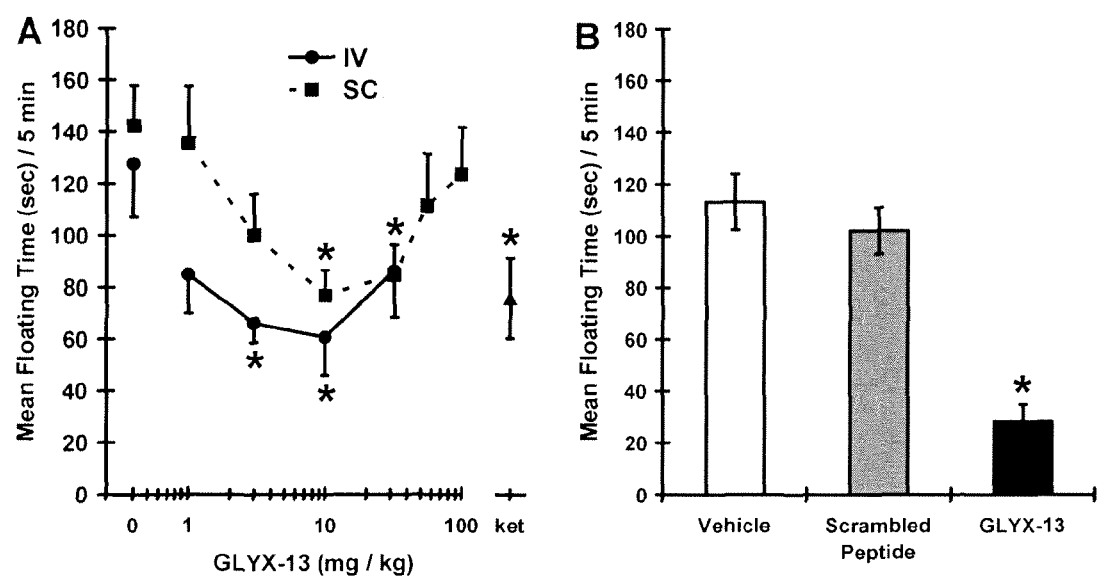
FIG. 12 shows GLYX-13 produced an acute antidepressant-like effect in the Porsolt test.

GLYX-13 (3-10 mg/kg, IV; 10-30 mg/kg, SC) significantly (P<0.05) reduced floating times in the Porsolt test by both the IV and SC routs of administration as did ketamine (10 mg/kg IP) (FIG. 12A). A scrambled peptide control (TPTP-NH2; 3 mg/kg IV) had no significant effect (FIG. 12B).

FIGS. 12A and 12B show that GLYX-13 produced an acute antidepressant-like effect in the Porsolt test. Mean (±SEM) time (sec) spent immobile in the Porsolt test in 3-month old male Sprague Dawley rats were dosed with (A) intravenous GLYX-13 (1, 3, 10, 30 mg/kg), subcutaneous GLYX (1, 3, 10, 30, 56, 100 mg/kg), ketamine (10 mg/kg IP), or saline vehicle; (B) GLYX-13 (3 mg/kg IV), scrambled peptide (3 mg/kg IV) or saline vehicle. All animals were tested 20-60 min post dosing. Animals received a 15-min training swim session one day before dosing. N=7-12 per group. * P<0.05, Fisher's PLSD post hoc vs. vehicle.

Figure 13:
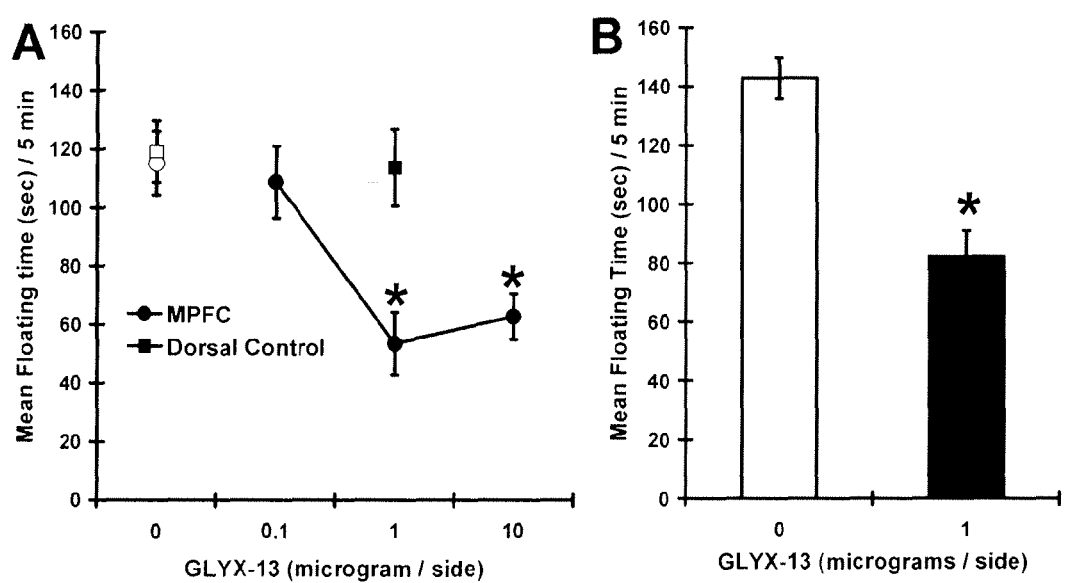
FIG. 13 shows the antidepressant-like effects of GLYX-13 were localized to the medial prefrontal cortex.

MPFC but not motor cortex injections of GLYX-13 (1 and 10 μg/side) reduced floating time in the Porsolt test 20 min post dosing P<0.05) (FIG. 13A). Reduction in floating time was still apparent two weeks following MPFC injection of GLYX-13 (1 μg/side) in an independent group of animals (P<0.0001) (FIG. 13B).

FIGS. 13A and 13B show that the antidepressant-like effects of GLYX-13 were localized to the medial prefrontal cortex. Mean (±SEM) time (sec) spent immobile in the Porsolt test in 3 month old male Sprague Dawley rats implanted with medial prefrontal or motor cortex (dorsal control) cannulae and injected with GLYX-13 (0.1, 1, 10 μg/side) or sterile saline vehicle (0.5 μlL/1 min) 20 min (A) or 2 weeks post-dosing (B). Animals received a 15 min training swim session one day before dosing. N=9-10 per group. * P<0.05, Fisher PLSD vs. vehicle.

Drug Discrimination

Figure 14:
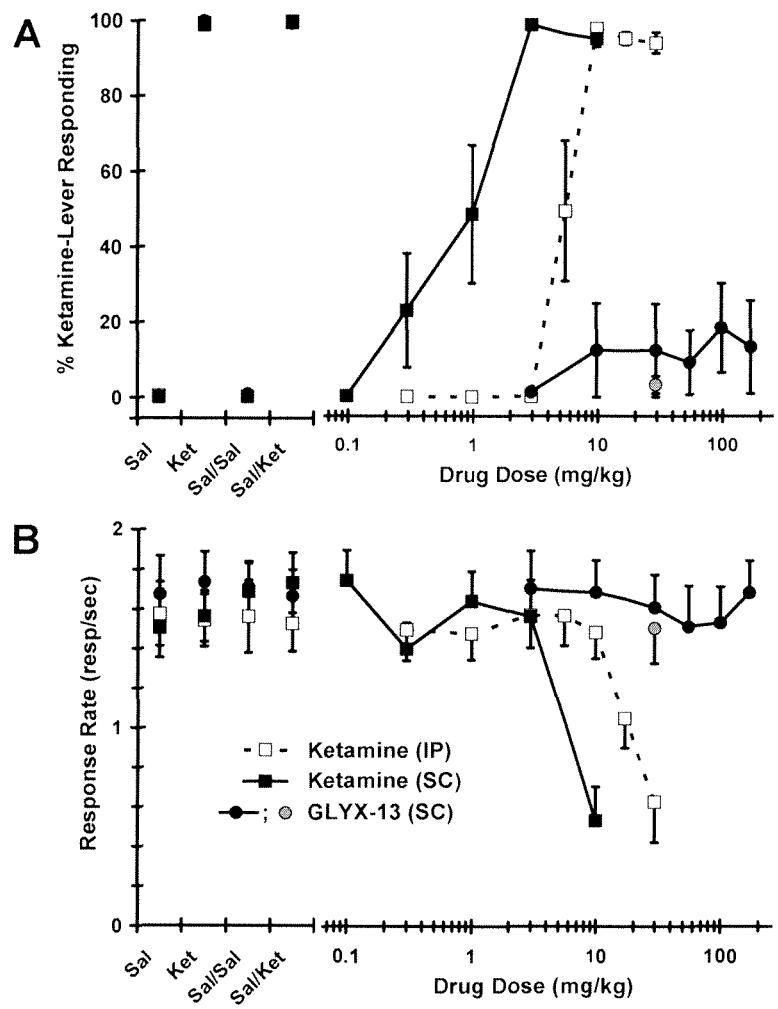
FIG. 14 shows GLYX-13 did not exhibit any ketamine-like discriminative stimulus effects or suppress operant responding.

As shown in FIG. 14, (A) animals treated with SC GLYX-13 over the dose range 3-156 mg/kg did not show any ketamine-like discriminative stimulus effects, whereas animals treated with ketamine IP (5.6-30 mg/kg; P<0.05) or SC (1-10 mg/kg; P<0.05) produced dose-dependent increases in ketamine-lever selection (B) GLYX-13 (3-156 mg/kg, SC) did not suppress operant responding at any dose (all Ps>0.05) unlike ketamine at the higher doses IP (30 mg/kg; P<0.05) or SC (10 mg/kg; P<0.05).

FIGS. 14A and 14B shows GLYX-13 did not exhibit any ketamine-like discriminative stimulus effects or suppress operant responding. Mean (±SEM) (A) percentage ketamine-lever responding and (B) rates of responding for different doses of ketamine (IP and SC) and GLYX-13 (SC) in rats trained to discriminate 10 mg/kg ketamine, IP, from saline. Values above Sal and Ket are the results of control tests conducted before testing each dose response curve. Values above Sal/Sal and Sal/Ket are the results of similar control tests performed following administration of 2 mL saline SC, 30 min before the session start to mimic conditions of GLYX-13 testing. N=6-8 per group.

Prepulse Inhibition and Conditioned Place Preference

Figure 15:
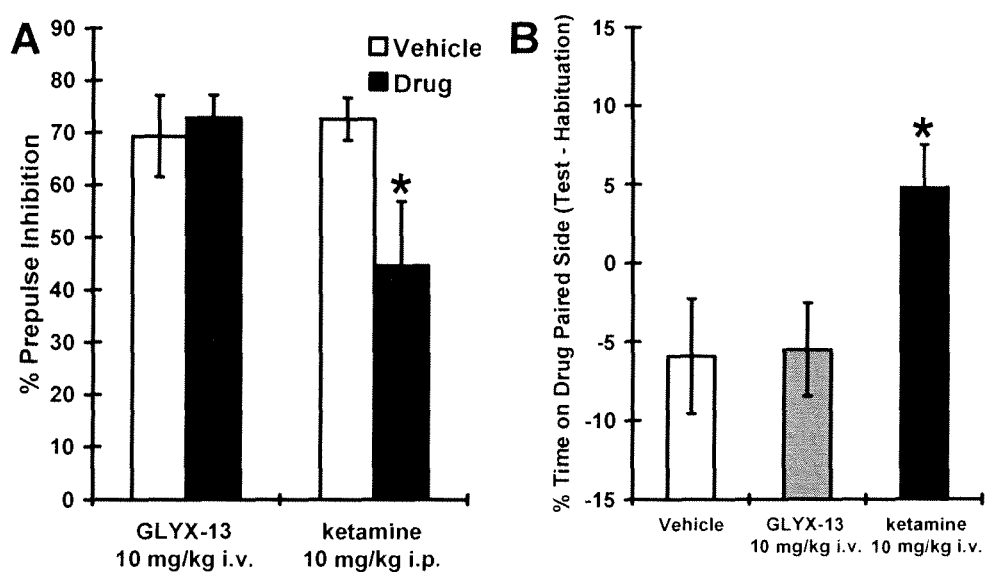
FIG. 15 shows GLYX-13 did not affect prepulse inhibition, or induce conditioned place preference.

Ketamine decreased prepulse inhibition (FIG. 15A) an indicator of dissociative effects, and induced conditioned place preference (FIG. 15B) an indicator of abuse potential, all P<0.05. In contrast, GLYX-13 did not exhibit either of these effects (FIG. 15) suggesting a lack of dissociative effects and abuse potential.

FIGS. 15A and 15B shows GLYX-13 did not affect prepulse inhibition, or induce conditioned place preference. Ketamine (but not GLYX-13) decreased prepulse inhibition (Panel A), and induced conditioned place preference (Panel B) in 2-3 month old male Sprague-Dawley rats, N=8-10 per group, pretreated with either GLYX-13 (10 mg/kg IV) and tested 15 min following injection, or ketamine (10 mg/kg IP) or saline vehicle (1 mg/mL IV or IP respectively), tested immediately post injection for prepulse inhibition. N=8-10 per group. * P<0.05, Fisher PLSD vs. vehicle.

Signal Transduction in Response to GLYX-13 or Ketamine

Figure 16:
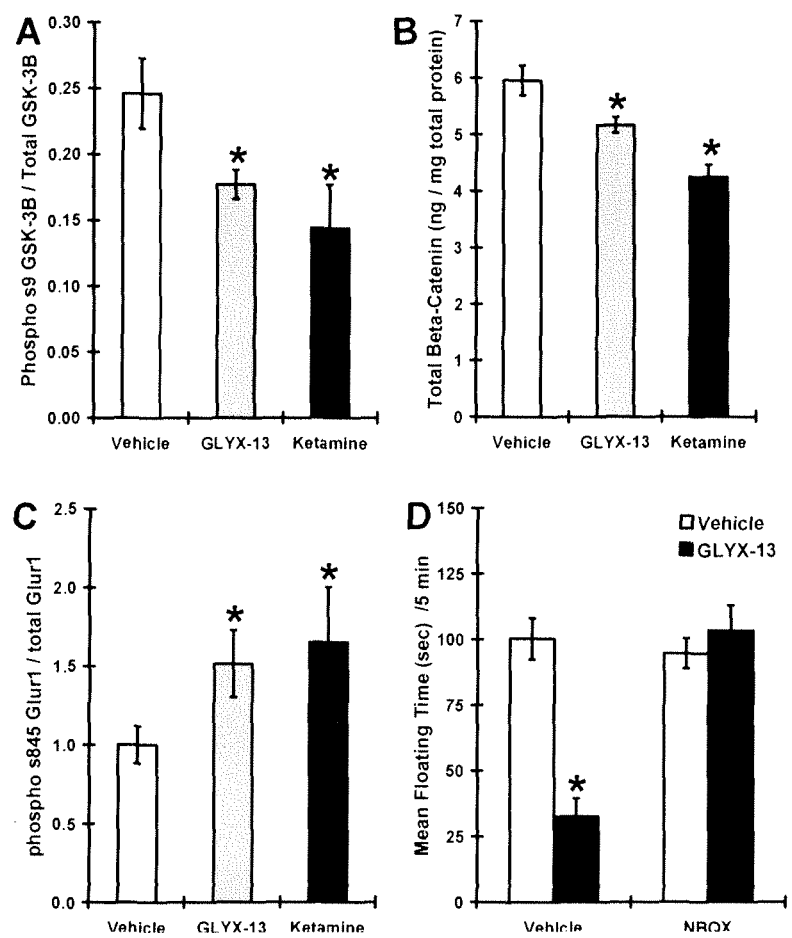
FIG. 16 shows GLYX-13 up regulated GluR1 Phosphoserine 845 and its antidepressant-like effects are blocked by AMPA receptor antagonism similar to ketamine.

GLYX-13 and ketamine reduced phosphoserine-9 GSK-3β/total GSK-3β ratio (P<0.05) (FIG. 14A) and total ⊕-catenin (FIG. 16B). Phosphoserine-845 GluR1/total GluR1 ratio was increased in the medial prefrontal cortex of animals pretreated with GLYX-13 or ketamine 24 hours prior to sacrifice (P<0.05)(FIG. 16C). As has also been reported for ketamine, the AMPA receptor antagonist NBQX blocked the antidepressant-like effect of GLYX-13 in the Porsolt test (FIG. 16D (P<0.0001).

FIGS. 16A, 16B, 16C, and 16D show GLYX-13 up regulated GluR1 Phosphoserine 845 and its antidepressant-like effects are blocked by AMPA receptor antagonism similar to ketamine. Mean (±SEM) (A) Protein levels of (A) Phosphoserine 9 GSK-3β/total GSK-3β, (B) Total Catenin, (C) Phosphoserine 845 GluR1/Total Glur1 in medial prefrontal cortex of 3 month old male Sprague Dawley rats dosed with GLYX-13 (3 mg/kg IV), ketamine (10 mg/kg IV) or vehicle 24 hrs before sacrifice; (D) Floating time in the Porsolt test in animals pretreated with the AMPA receptor antagonist NBQX (10 mg/kg IP) before GLYX-13 (3 mg/kg IV) dosing and tested 1 hr post dosing. N=4-11 per group. * P<0.05, Fisher PLSD vs. vehicle.

Functional Affinity of GLYX-13 to the NMDA Receptor

Figure 17:
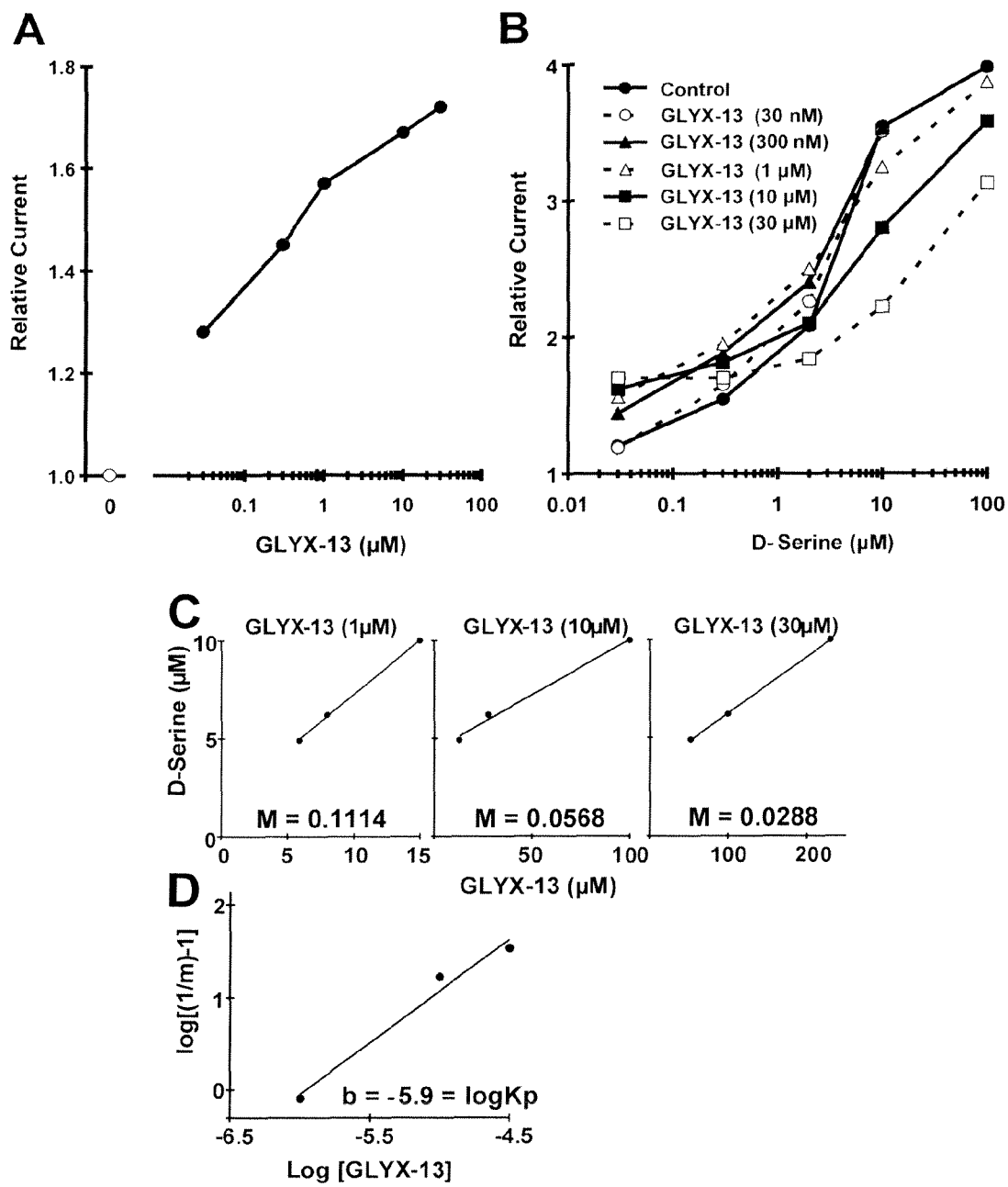
FIG. 17 shows GLYX-13 acted as a partial agonist at the glycine site of the NMDA receptor.

Because partial agonists may bind to receptors without producing full effects, radioligand binding affinity may reflect artifactually potent affinity. Thus, the Stephenson method was used to evaluate the functional affinity of GLYX-13 for the NMDAR. Precision in the calculations was improved by repeating the procedure for three concentrations of GLYX-13 (FIG. 17, Panel B), from which a series of pairs of equiactive concentrations of D-serine (ordinate) and D-serine+GLYX-13 (axis) were plotted (FIG. 17, Panel C). Plotting log(1/slope−1) vs. log [GLYX-13] yielded a line (FIG. 17, Panel D) with pKp as intercept. The use of this method requires that the partial agonist have much less intrinsic activity than full agonists at the site in order that the ratio εP/εA may be ignored. GLYX-13 was found to have 23% of the activity of D-serine in the hippocampal slice assay (FIG. 17, Panels A and B), fulfilling the requirement that partial agonist activity be 75% or less that of a full agonist, and preferably 25% or less (Kenakin T P (1997) Pharmacologic Analysis of Drug-Receptor Interaction (New York)).

FIGS. 17A, 17B, 17C, and 17D shows GLYX-13 acted as a partial agonist at the glycine site of the NMDA receptor. (A-B) Pharmacologically isolated NMDA receptor current was measured from hippocampal slices to determine (A) the percent intrinsic activity of GLYX-13 as compared to the endogenous ligand which is approximately 23%, and (B) D-Serine concentration-response in the absence and in the presence of increasing concentrations of GLYX-13. (C) Plots of equieffective concentrations of D-Serine in the absence and presence of 1, 10 and 30 μM GLYX-13. (D) Using the slopes (m) from the relationships in Panel B, a plot of log [(1/m)−1] vs. log [GLYX-13] yields x-intercept of log $K_{GLYX-13}$ (Stephenson R P (1956) A modification of receptor theory. Br J Pharmacol Chemother 11(4):379-393).

Drug distribution studies following IV administration of GLYX-13 at 3 and 10 mg/kg revealed $C_{max}$ within the CSF compartment of 0.06 and 0.2 μM, respectively (FIG. 18). These concentrations were demonstrated to be pharmacologically relevant in the slice current studies (FIGS. 17A and 17B).

FIG. 18 shows mean CSF concentrations of GLYX-13 following IV administration of 3 or 10 mg/kg. N=3 rats/group. GLYX-13 CSF levels were measured by LC/MS/MS.

These results show that the NMDA receptor glycine-site partial agonist, GLYX-13, causes a robust, long-lasting antidepressant-like effect with rapid onset in rats. Moreover, at doses that produced antidepressant-like effects, or doses 10-fold higher, GLYX-13, unlike ketamine, essentially did not cause dissociation-like effects in the prepulse inhibition test. GLYX-13 also essentially did not demonstrate ketamine-like discriminative stimulus effects or abuse potential in the conditioned place preference test. GLYX-13, 10 mg/kg SC, was active in the Porsolt test. At the highest dose evaluated, 156 mg/kg SC, in the drug discrimination assay, GLYX-13 was essentially without effect, making the therapeutic index at least 170:10, or 17.

EQUIVALENTS

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, parameters, descriptive features and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

What is claimed is:

1. A method for treating bipolar disorder in a patient in need thereof, comprising administering to said patient about 1 mg/kg to about 10 mg/kg of a compound represented by:

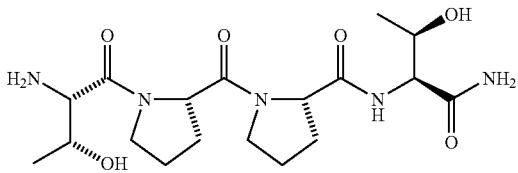

or a pharmaceutically acceptable salt thereof.

2. The method of claim 1, comprising administering the dose every week or every two weeks to said patient.

3. The method of claim 1, wherein the administration of a single dose is effective for up to 4 days.

4. The method of claim 1, further comprising administering another antidepressant drug.

5. The method of claim 2, further comprising administering another antidepressant drug.

6. A method for treating bipolar disorder in a patient in need thereof, comprising administering to said patient a pharmaceutically acceptable composition comprising:

about 1 mg/kg to about 10 mg/kg dose of a compound represented by:

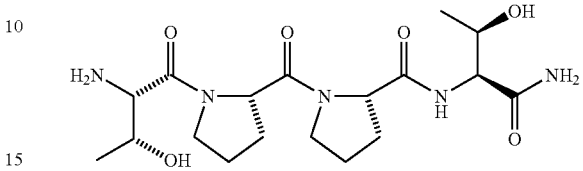

or pharmaceutically acceptable salts thereof; and an excipient.

7. The method of claim 1, comprising administering to said patient about 5 mg/kg of the compound.

* * * * *

SEQUENCE LISTING

```
<160> NUMBER OF SEQ ID NOS: 13

<210> SEQ ID NO 1
<211> LENGTH: 11
<212> TYPE: PRT
<213> ORGANISM: Artificial
<220> FEATURE:
<223> OTHER INFORMATION: Synthetic Peptide

<400> SEQUENCE: 1

Lys Ala Ser Gln Asp Val Ser Thr Thr Val Ala
1               5                   10

<210> SEQ ID NO 2
<211> LENGTH: 7
<212> TYPE: PRT
<213> ORGANISM: Artificial
<220> FEATURE:
<223> OTHER INFORMATION: Synthetic Peptide

<400> SEQUENCE: 2

Ser Ala Ser Tyr Arg Tyr Thr
1               5

<210> SEQ ID NO 3
<211> LENGTH: 9
<212> TYPE: PRT
<213> ORGANISM: Artificial
<220> FEATURE:
```

<223> OTHER INFORMATION: Synthetic Peptide

<400> SEQUENCE: 3

Gln Gln His Tyr Ser Thr Pro Pro Thr
1               5

<210> SEQ ID NO 4
<211> LENGTH: 13
<212> TYPE: PRT
<213> ORGANISM: Artificial
<220> FEATURE:
<223> OTHER INFORMATION: Synthetic Peptide

<400> SEQUENCE: 4

Val Tyr Tyr Ser Gln Gln His Tyr Ser Thr Pro Pro Thr
1               5                   10

<210> SEQ ID NO 5
<211> LENGTH: 17
<212> TYPE: PRT
<213> ORGANISM: Artificial
<220> FEATURE:
<223> OTHER INFORMATION: Synthetic Peptide

<400> SEQUENCE: 5

Glu Asp Leu Ala Val Tyr Tyr Ser Gln Gln His Tyr Ser Thr Pro Pro
1               5                   10                  15

Thr

<210> SEQ ID NO 6
<211> LENGTH: 22
<212> TYPE: PRT
<213> ORGANISM: Artificial
<220> FEATURE:
<223> OTHER INFORMATION: Synthetic Peptide

<400> SEQUENCE: 6

Ser Val Gln Ala Glu Leu Asp Leu Ala Val Tyr Tyr Ser Gln Gln His
1               5                   10                  15

Tyr Ser Thr Pro Pro Thr
            20

<210> SEQ ID NO 7
<211> LENGTH: 26
<212> TYPE: PRT
<213> ORGANISM: Artificial
<220> FEATURE:
<223> OTHER INFORMATION: Synthetic Peptide

<400> SEQUENCE: 7

Phe Thr Ile Ser Ser Val Gln Ala Glu Leu Asp Leu Ala Val Tyr Tyr
1               5                   10                  15

Ser Gln Gln His Tyr Ser Thr Pro Pro Thr
            20                  25

<210> SEQ ID NO 8
<211> LENGTH: 13
<212> TYPE: PRT
<213> ORGANISM: Artificial
<220> FEATURE:
<223> OTHER INFORMATION: Synthetic Peptide

<400> SEQUENCE: 8

Gln Gln His Tyr Ser Thr Pro Pro Thr Phe Gly Gly Gly
1               5                   10

```
<210> SEQ ID NO 9
<211> LENGTH: 17
<212> TYPE: PRT
<213> ORGANISM: Artificial
<220> FEATURE:
<223> OTHER INFORMATION: Synthetic Peptide

<400> SEQUENCE: 9

Gln Gln His Tyr Ser Thr Pro Pro Thr Phe Gly Gly Gly Thr Lys Leu
1               5                   10                  15

Glu

<210> SEQ ID NO 10
<211> LENGTH: 11
<212> TYPE: PRT
<213> ORGANISM: Artificial
<220> FEATURE:
<223> OTHER INFORMATION: Synthetic Peptide
<220> FEATURE:
<221> NAME/KEY: DISULFID
<222> LOCATION: (1)..(11)

<400> SEQUENCE: 10

Cys Gln Gln His Tyr Ser Thr Pro Pro Thr Cys
1               5                   10

<210> SEQ ID NO 11
<211> LENGTH: 11
<212> TYPE: PRT
<213> ORGANISM: Artificial
<220> FEATURE:
<223> OTHER INFORMATION: Synthetic Peptide

<400> SEQUENCE: 11

Ser Gln Gln His Tyr Ser Thr Pro Pro Thr Ser
1               5                   10

<210> SEQ ID NO 12
<211> LENGTH: 5
<212> TYPE: PRT
<213> ORGANISM: Artificial
<220> FEATURE:
<223> OTHER INFORMATION: Synthetic Peptide

<400> SEQUENCE: 12

Gln Gln His Tyr Ser
1               5

<210> SEQ ID NO 13
<211> LENGTH: 4
<212> TYPE: PRT
<213> ORGANISM: Artificial
<220> FEATURE:
<223> OTHER INFORMATION: Synthetic Peptide

<400> SEQUENCE: 13

Thr Pro Pro Thr
1
```